United States Patent [19]

Narula et al.

[11] Patent Number: 5,068,363

[45] Date of Patent: Nov. 26, 1991

[54] CYCLOHEXENYLMETHLOXABICYCLOOC-TANES, PROCESSES FOR PREPARING SAME, INTERMEDIATES USED IN SAID PROCESSES AND ORGANOLEPTIC USES OF SAID CYCLOHEXENYLMETHLOXABICYCLOOC-TANES AND INTERMEDIATES THEREFOR

[75] Inventors: Anubhav P. S. Narula, Hazlet; John J. De Virgilio, Freehold, both of N.J.

[73] Assignee: International Flavors & Fragrances Inc., New York, N.Y.

[21] Appl. No.: 588,732

[22] Filed: Sep. 27, 1990

[51] Int. Cl.$^5$ ............................................. C07D 313/06
[52] U.S. Cl. .................... 549/355; 549/398; 568/446; 568/816
[58] Field of Search ............... 549/355, 398; 568/446, 568/816

[56] References Cited

U.S. PATENT DOCUMENTS

| | | | |
|---|---|---|---|
| 4,195,100 | 3/1980 | Sprecker et al. | 549/397 |
| 4,224,176 | 9/1980 | Sprecker et al. | 512/13 |
| 4,267,067 | 5/1981 | Sprecker et al. | 252/174.11 |
| 4,269,862 | 5/1981 | Sprecker et al. | 426/536 |

OTHER PUBLICATIONS

"Perfume and Flavor Chemicals" (Aroma Chemicals), 1969 (published by the author), Monograph 616.

Primary Examiner—James H. Reamer
Attorney, Agent, or Firm—Arthur L. Liberman

[57] ABSTRACT

Described are cyclohexenylmethyloxabicyclooctanes defined according to the generic structures:

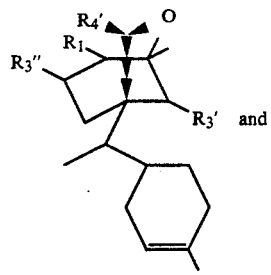

and

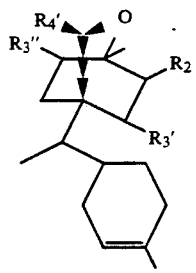

as well as intermediates for producing same defined according to the generic structures:

and (Abstract continued on next page.)

wherein $R_1$, $R_2$, $R_3'$, and $R_3''$ are each hydrogen or methyl with the provisos:
(i) one or both of $R_1$ and $R_2$ is methyl;
(ii) when $R_1$ and $R_2$ are both methyl then $R_3'$ and $R_3''$ each represents hydrogen;
(iii) one of $R_3'$ and $R_3''$ is methyl and the other is hydrogen or $R_3'$ and $R_3''$ both represent hydrogen; and
(iv) when $R_3'$ and $R_3''$ are both methyl then $R_1$ is methyl and $R_2$ is hydrogen;

and $R_4'$ is hydrogen or $C_1$-$C_5$ alkyl. Also described are the organoleptic uses of said cyclohexenylmethyloxabicyclooctanes wherein implementing or enhancing the aroma of perfume compositions, colognes and perfumed articles.

4 Claims, 9 Drawing Sheets

GLC PROFILE FOR EXAMPLE I.

GLC PROFILE FOR EXAMPLE II.

FIG. 4 NMR SPECTRUM FOR EXAMPLE II.

GLC PROFILE FOR EXAMPLE III

FIG. 6 NMR SPECTRUM FOR EXAMPLE III.

GLC PROFILE FOR EXAMPLE IV.

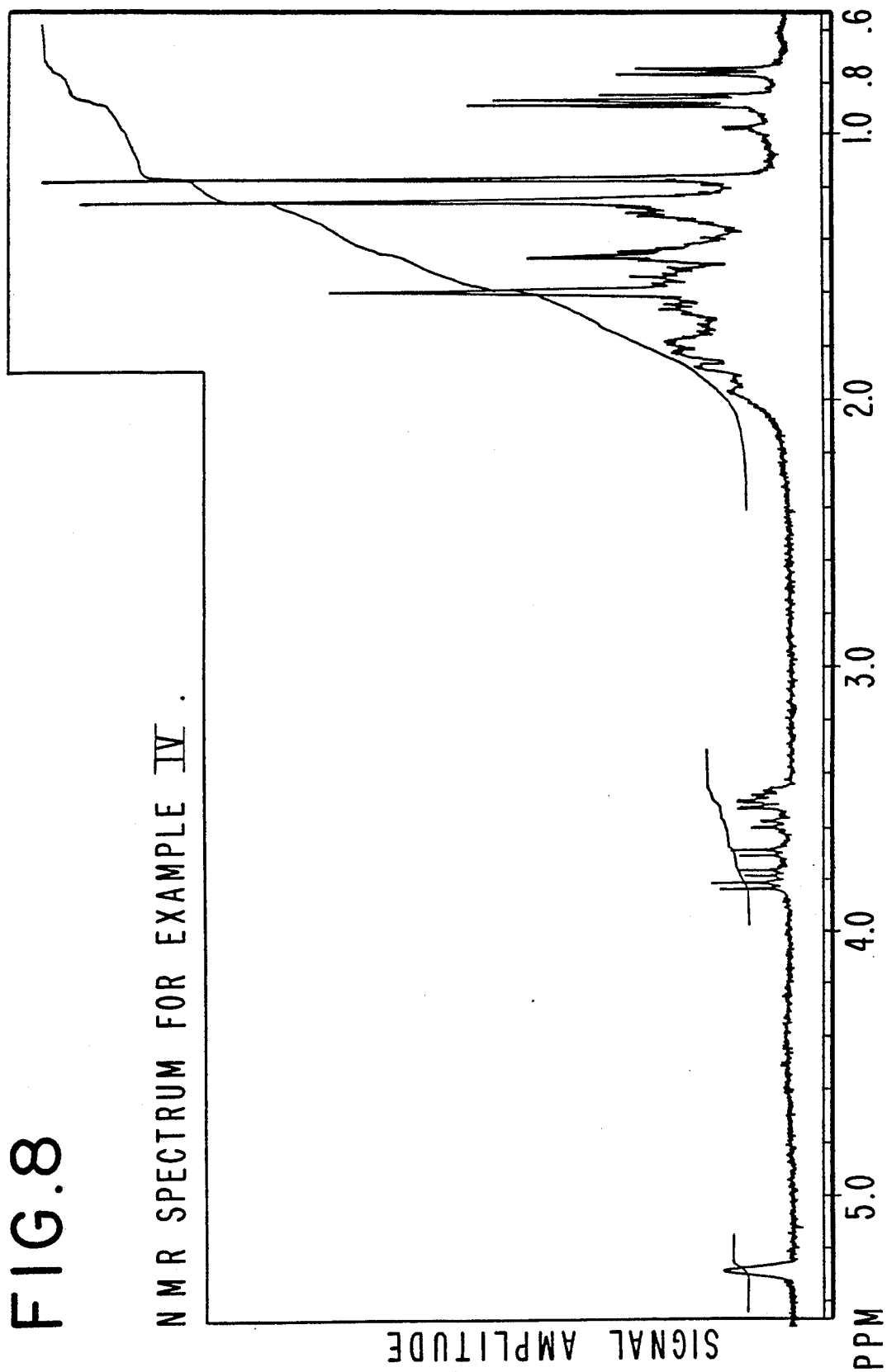
FIG. 8 NMR SPECTRUM FOR EXAMPLE IV.

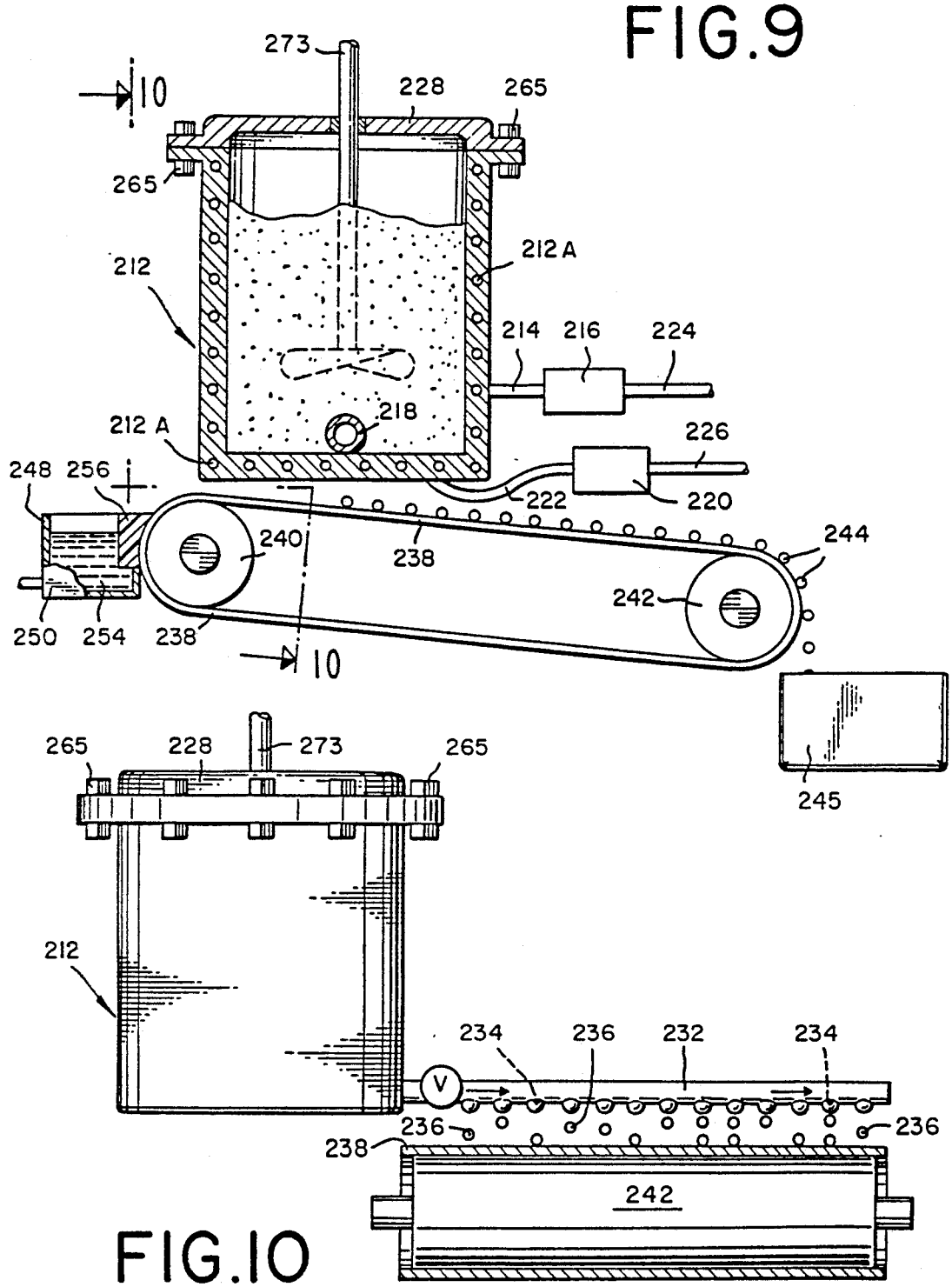

CYCLOHEXENYLMETHLOXABICYCLOOCTANES, PROCESSES FOR PREPARING SAME, INTERMEDIATES USED IN SAID PROCESSES AND ORGANOLEPTIC USES OF SAID CYCLOHEXENYLMETHLOXABICYCLOOCTANES AND INTERMEDIATES THEREFOR

BACKGROUND OF THE INVENTION

This invention relates to cyclohexenylmethyloxabicyclooctanes defined according to the generic structures:

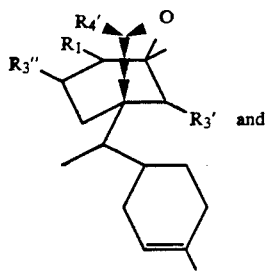

as well as intermediates for producing same defined according to the generic structures:

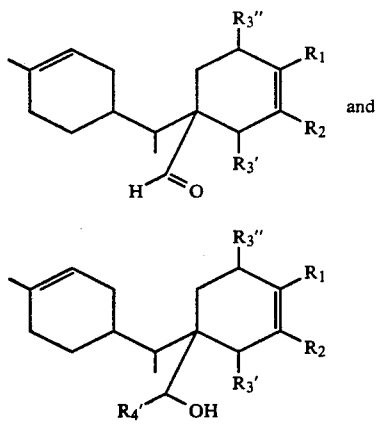

as well as organoleptic uses of said cyclohexenylmethyloxabicyclooctanes and intermediates therefor in augmenting or enhancing the aroma of perfume compositions, colognes and perfumed articles, wherein $R_1$, $R_2$, $R_3'$ and $R_3''$ each represents hydrogen or methyl with the provisos:

(i) one or both of $R_1$ and $R_2$ represents methyl;

(ii) when $R_1$ and $R_2$ are both methyl, then $R_3'$ and $R_3''$ are both hydrogen;

(iii) one of $R_3'$ and $R_3''$ is methyl and the other is hydrogen or $R_3'$ and $R_3''$ both represent hydrogen; and (iv) when $R_3'$ or $R_3''$ represents methyl then $R_1$ is methyl and $R_2$ is hydrogen and $R_4'$ is hydrogen or $C_1$-$C_5$ alkyl.

There has been considerable work performed relating to substances which can be used to impart, modify, augment or enhance fragrances with regard to perfume compositions, perfumed articles and colognes. Earthy, green, animalic and musky aromas with earthy and green topnotes are particularly desirable in augmenting or enhancing the aroma of perfume compositions, colognes and perfumed articles (e.g., solid or liquid anionic, cationic, nonionic or zwitterionic detergents, fabric softener compositions, fabric softener articles, hair preparations, cosmetic powders and perfumed polymers.

Oxabicyclooctanes having various substituents are known for use in perfumery. Thus, Arctander in "Perfume and Flavor Chemicals (Aroma Chemicals)", Vol. I, 1969 at monograph No. 616 describes 1,8-cineole having the structure:

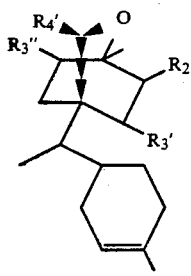

as being useful in perfumery and in flavor compositions. Thus, Arctander states, regarding 1,8-cineole:

"Fresh, diffusive, camphoraceous-cool odor of poor tenacity. Sweet and fresh, cool-camphoraceous taste and cool mouthfeel unless very highly concentrated. Widely used in perfume compositions for its refreshing effect in herbaceous type fragrances, Lavender, New Mown Hay, Fougere, etc. and in medicinal type odors for soap and household products. Also, in masking odors for industrial purposes, unless Eucalyptus oil must be used for its lower cost.

This oxide has found increased usage during the 1965/66 period of abnormally high prices for Lavandin and Spike Lavender oils.

The odor of Eucalyptus is, in some countries, rated synonymous with masking odors for lavatories, etc., a fact which has an unquestionable psychological effect, causing people to reject the odor of Eucalyptus for oral-hygienic purposes, etc. Similar viewpoints has been observed about the use of Methylsalicylate in dentifrice in many European countries. Peculiarly enough, Methylsalicylate is still a popular candy-, soft-drink- and toothpaste flavor in the U.S.A., where the ester at the same time is used as a masking agent in toilet-bowl cleaners!

The 'olfactory association' is quite human and common, but it may at times completely destroy the chances of a chemical from its use in flavors or other field.

Eucalyptol is extensively used in flavor compositions, particularly in all types of preparations for oral hygiene, dentifrice, breath-sprays, mouthwashes, cough lozenges, pastilles, skin-rubbing lotions, inhalator fluids, etc.

It seems, however, that its use in skin rubbing lotions has hampered its popularity as a candy flavor in the U.S.A.

Normal use concentrations are about 1 to 15 ppm in the finished (flavored) product, but concentrations as high as 200 ppm are found in chewing gum."

Sprecker, et al. in U.S. Letters Pat. No. 4,269,862 at column 3, lines 30-33 discloses the genus of compounds defined according to the structure:

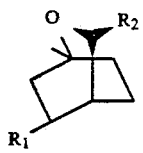

wherein $R_1$ is hydrogen or methyl and wherein $R_2$ is $C_1-C_5$ alkyl or alkenyl as having perfume utility. Furthermore, Sprecker, et al. discloses at column 4, lines 35-40 the compound having the structure:

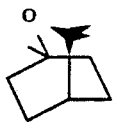

as having a minty, camphoraceous, woody and piney aroma useful in augmenting or enhancing the aroma of perfume compositions, colognes and perfumed articles.

Sprecker, et al. further discloses the reaction:

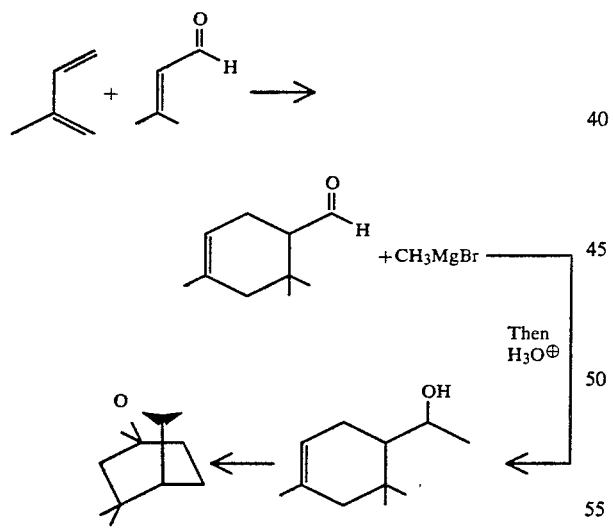

in preparing such oxabicyclooctane derivatives. Sprecker, et al., U.S. Letters Pat. No. 4,267,067 discloses the reaction:

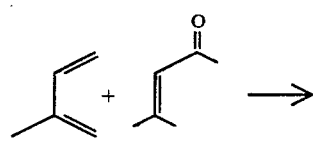

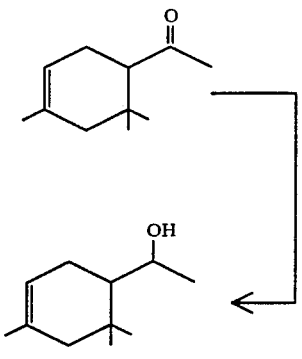

in preparing oxabicyclooctane derivatives useful in augmenting or enhancing the aroma of perfume compositions, colognes and articles.

Nothing in the prior art, however, discloses the cyclohexenylmethyloxabicyclooctanes of our invention or intermediates therefor or uses of said cyclohexenylmethyloxabicyclooctanes or intermediates therefor in augmenting or enhancing the aroma of perfume compositions., colognes and perfumed articles.

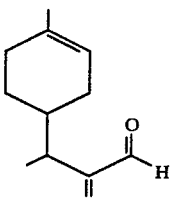

(Conditions:Carbowax column programmed at 220° C. isothermal).

Figure 2:
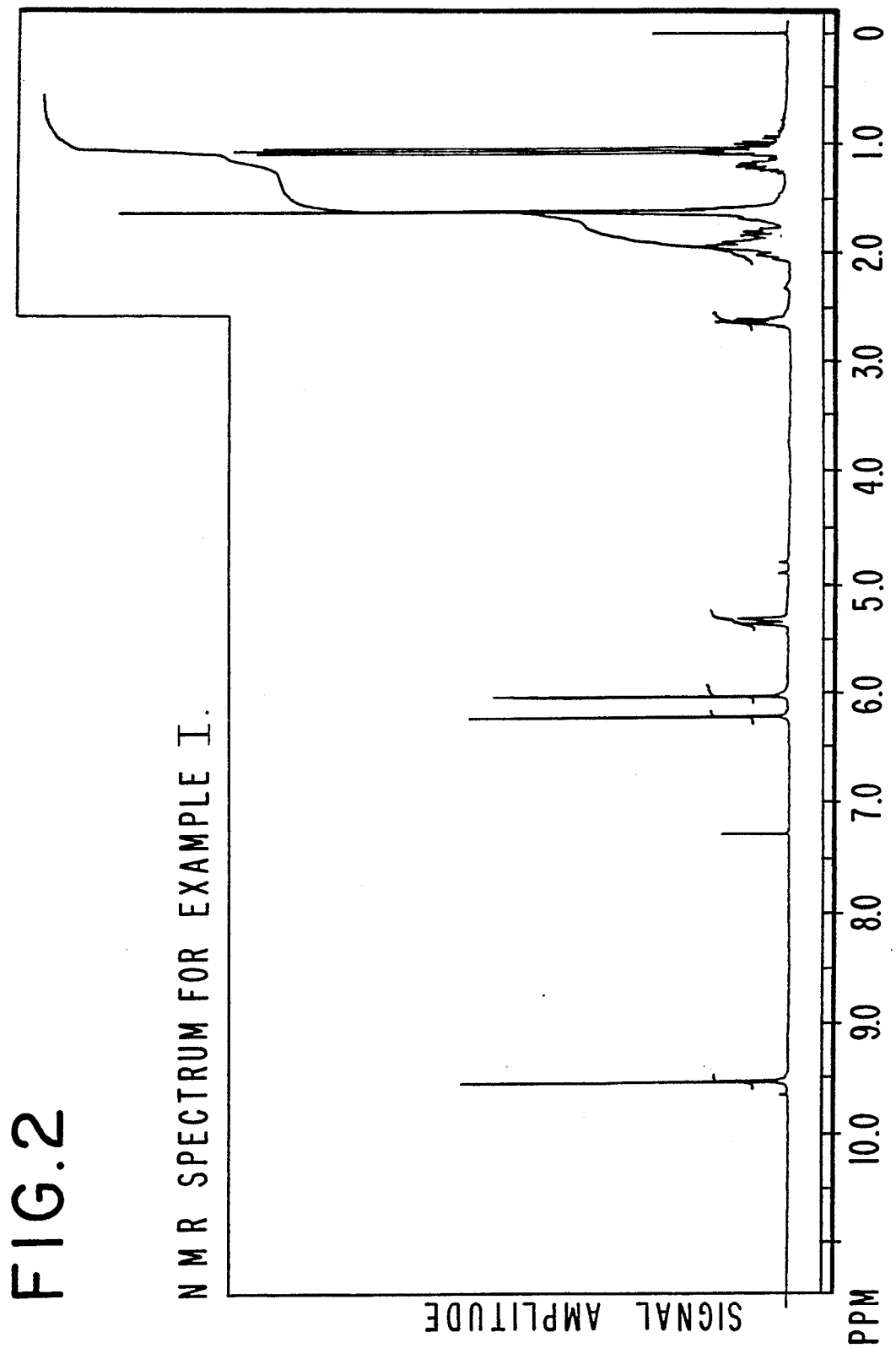

FIG. 2 is the NMR spectrum for the compound having the structure:

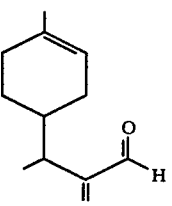

prepared according to Example I.

Figure 3:
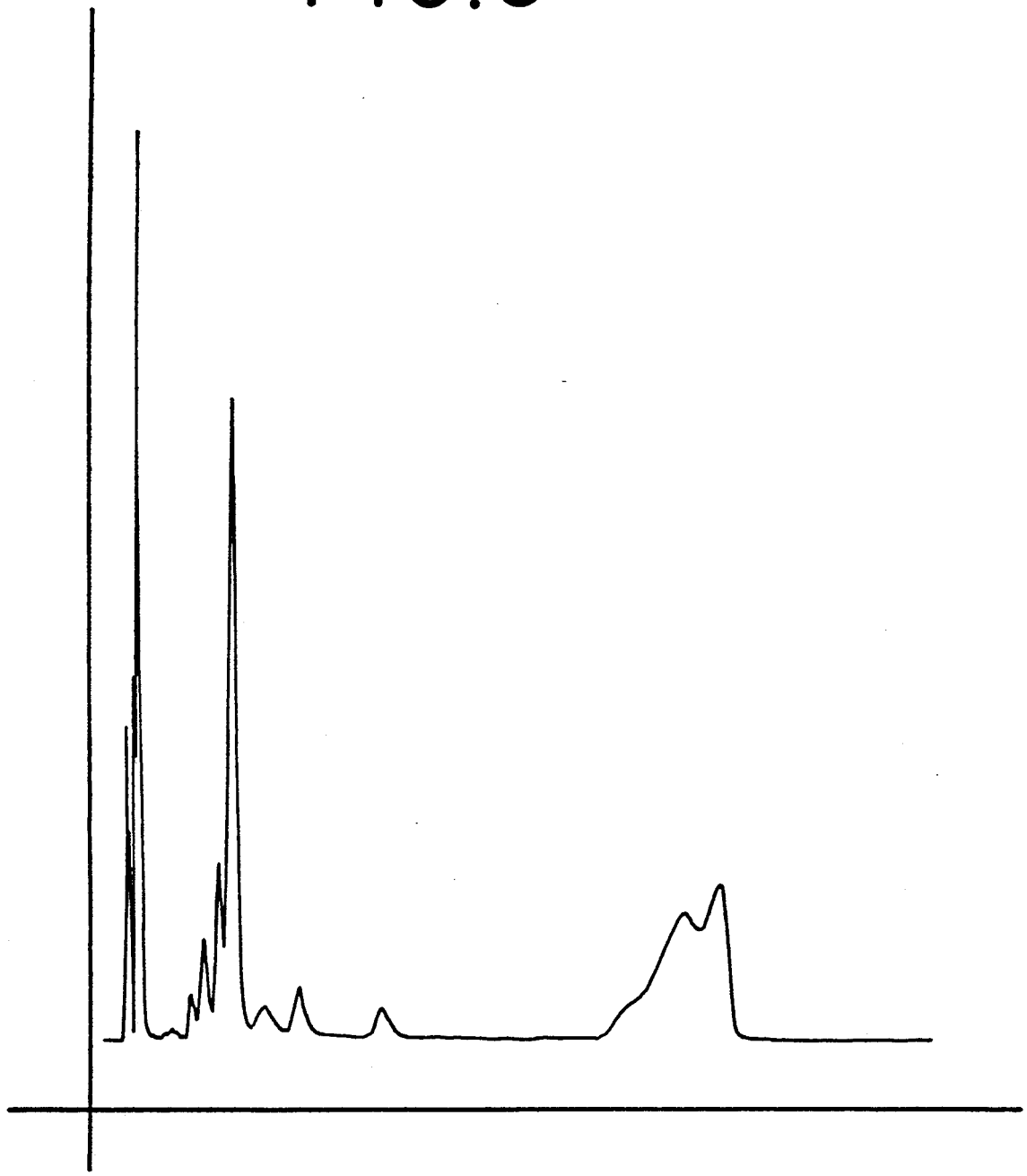

FIG. 3 is the GLC profile for the mixture of compounds having the structures:

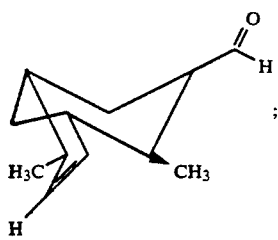

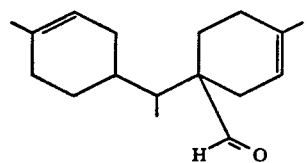

and

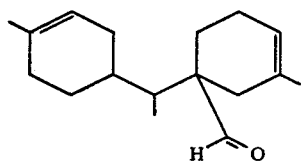

prepared according to Example II.
(Conditions:Carbowax column programmed at 220° C. isothermal).

Figure 4:
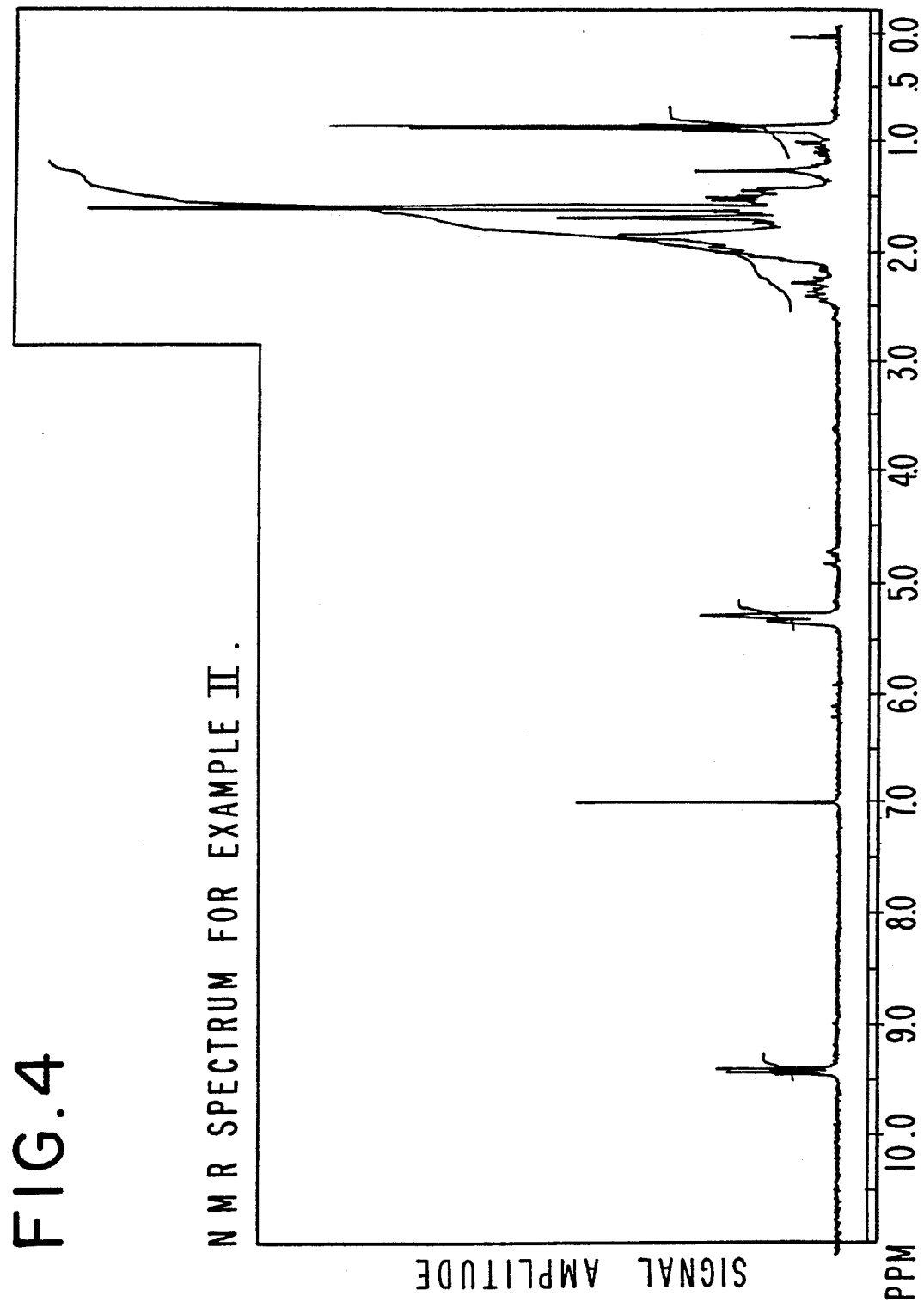

FIG. 4 is the NMR spectrum for the mixture of compounds having the structures:

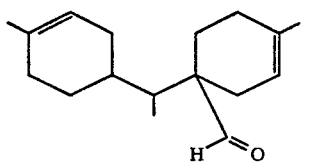

and

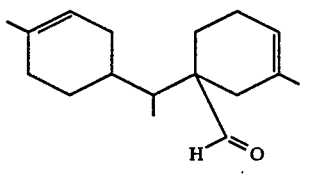

prepared according to Example II.

Figure 5:
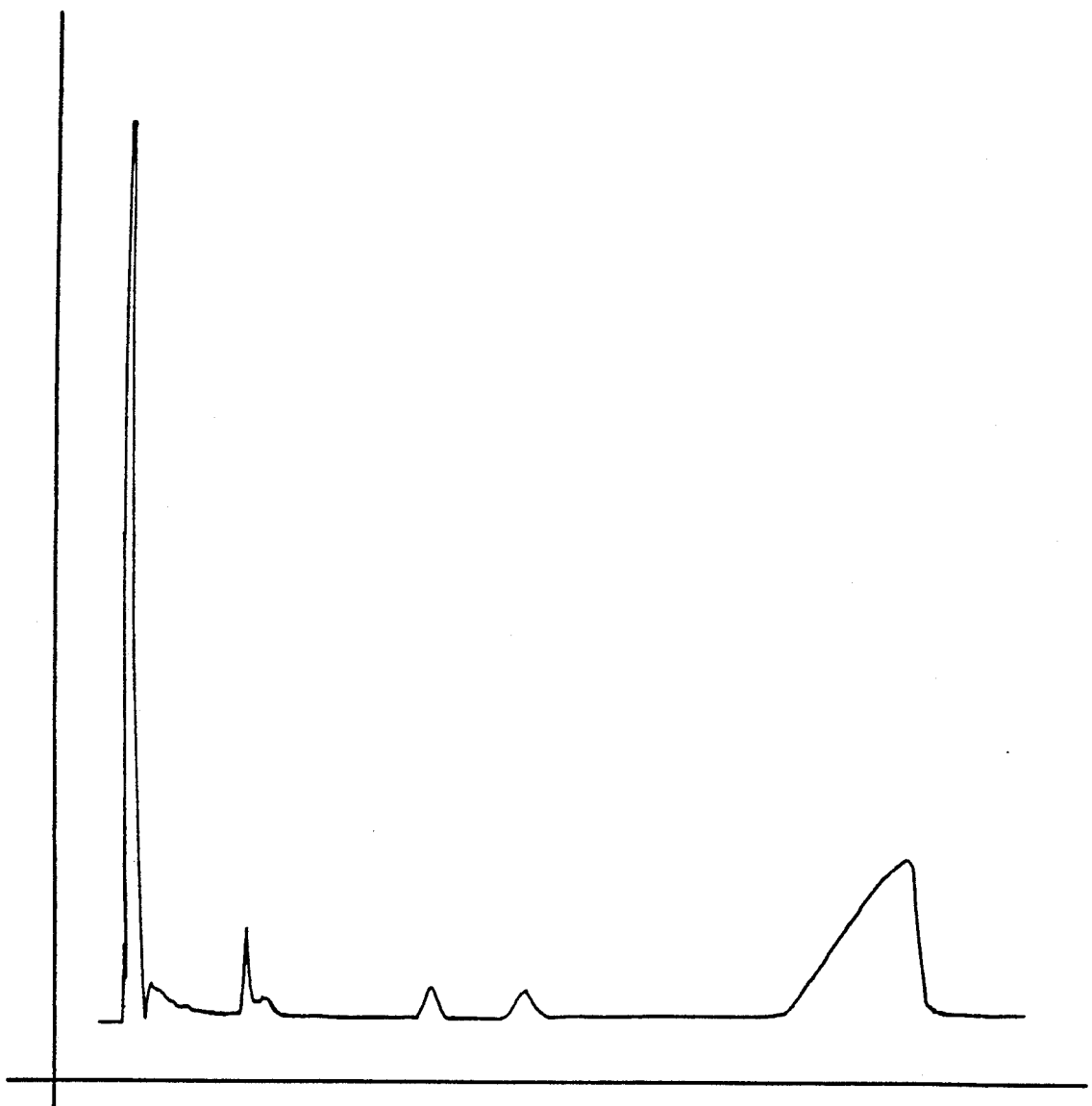

FIG. 5 is the GLC profile for the reaction product of Example III containing the compounds having the structures:

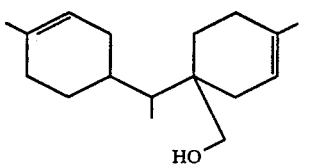

and

-continued

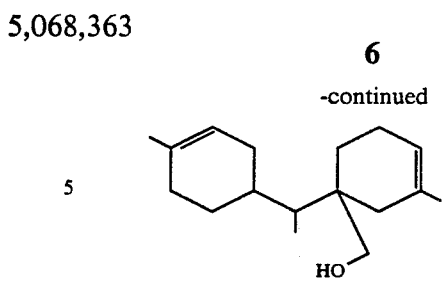

(Conditions:SE-30 column programmed at 220° C. isothermal).

Figure 6:
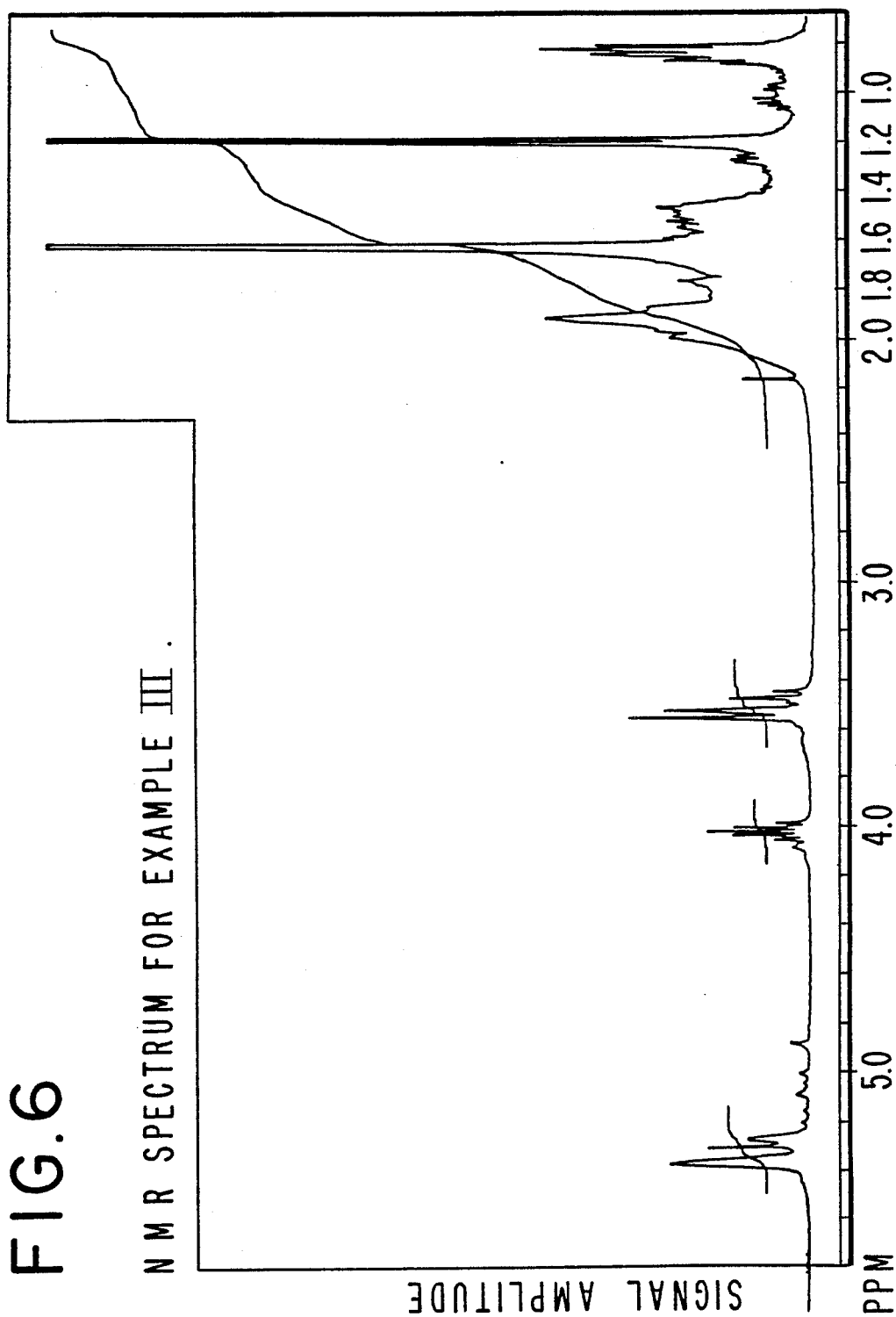

FIG. 6 is the NMR spectrum for the mixture of compounds having the structures:

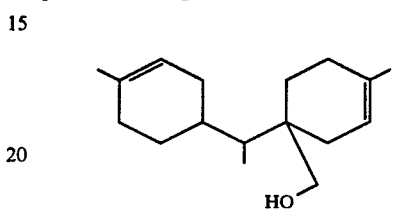

and

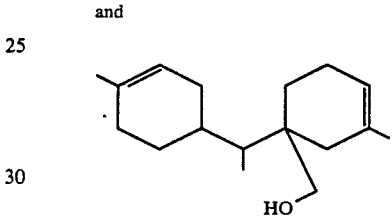

prepared according to Example III.

Figure 7:
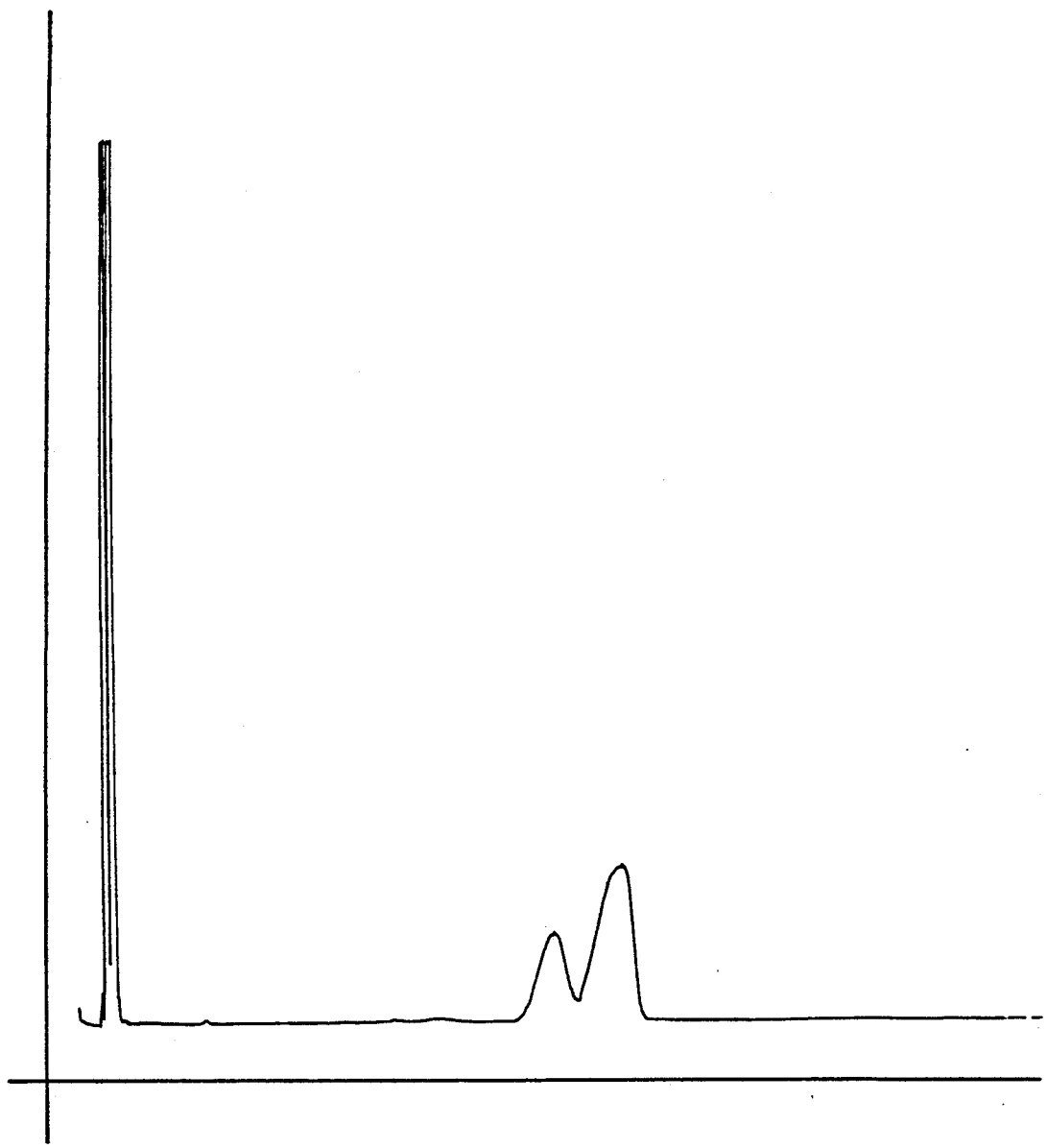

FIG. 7 is the GLC profile for the reaction product of Example IV containing the compounds having the structures:

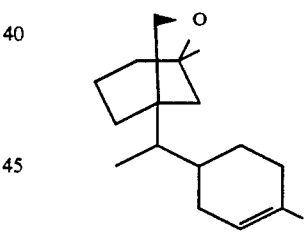

and

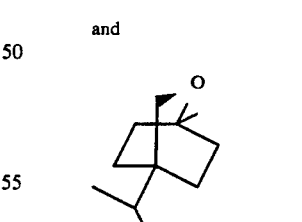

prepared according to Example IV.
(Conditions:SE-30 column programmed at 220° C. isothermal).

FIG. 8 is the NMR spectrum for the mixture of compounds having the structures:

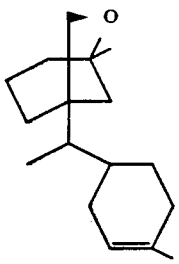

and

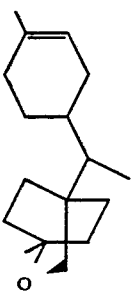

prepared according to according to Example IV.

FIG. 9 is a partial side elevation and partial sectional view of an apparatus useful for forming polymer pellets scented with one of the perfume compositions or perfumery materials of our invention.

FIG. 10 is a section taken on line 10—10 of FIG. 9.

DETAILED DESCRIPTION OF THE DRAWINGS

Referring to FIGS. 9 and 10, the apparatus used in producing polymeric fragrances containing one or more of the cyclohexenylmethyloxabicyclooctanes or intermediates therefor of our invention comprises a device for forming scented polyolefins (for example) pellets which comprises a vat 212 into which a mixture of polyolefins such as polyethylene and an aromatic substance or scented materials containing or consisting of at least one of the cyclohexenylmethyloxabicyclooctanes or intermediates therefor of our invention is placed. The container is closed by an air-tight lid 228 and clamped to the container by bolts 265. A stirrer 273 traverses the lid or cover 228 in air-tight manner and is rotated in a suitable manner. A surrounding cylinder 212 having heating coils 212-A which are supplied with electric current through cable 224 from a rheostat or control 216 or through cable 226 from a rheostat or control 220 is operated to maintain the temperature inside the container 212 such that the polyethylene or other thermoplastic polymer in the container will be maintained in the molten or liquid state. It has been found advantageous to employ a colorless, odorless polymer (e.g. polyethylene) with a viscosity ranging between 180 and 220 Saybolt seconds and having a melting point in the range of 200° F.–280° F. The heater 212-A is operated to maintain the upper portion of the container 212 within a temperature range of from 250° F. -350° F. The bottom portion of the container is heated by means of heating coils 212-A heated through a control 220 connected thereto through a connecting wire 226 to maintain the lower portion of the container 212 within a temperature range of from 250° F.–350° F.

Thus, polymer (e.g., polyolefin) added to the container 212 is heated from 10–12 hours whereafter a scent or aroma imparting material which contains or consists of at least one of the cyclohexenylmethyloxabicyclooctanes oxabicyclooctanes or intermediates therefor of our invention is quickly added to the melt. The material must be compatible with the polyolefin and forms a homogeneous liquid melt therewith. The scented material containing or consisting of at least one of the cyclohexenylmethyloxabicyclooctanes or intermediates therefor of our invention is of a type for the particular aroma desired and formulated specifically for the scenting purpose for which the polyolefin will be employed. Generally, about 10–30% by weight of scenting material is added to the polyolefin.

After the scent imparting material containing or consisting of at least one of the cyclohexenylmethyloxabicyclooctanes or intermediates therefor of our invention is added to the container 212, the mixture is stirred for a few minutes, for example, 5–15 minutes and maintained within the temperature ranges indicated previously by heating coils 212-A. The controls 216 and 220 are connected through cables 224 and 226 to a suitable supply of electric current for supplying power for heating purposes. As stated previously the controls 216 and 220 are connected to the heating coils 212-A through cables 214 (for control 216) and 222 (for control 220).

Thereafter, the valve "V" is opened permitting the mass to flow outwardly through conduit 232 having a multiplicity of orifices 234 adjacent to the lower side thereof. The outer end of the conduit 232 is closed so that the liquid polymer (e.g., polyolefin) and aroma imparting mixture (containing or oxabicyclooctanes or intermediates therefor of our invention) will continuously drop through the orifices 234 downwardly from the conduit 232. During this time the temperature of the polymer (e.g., polyolefin) and aroma mixture containing or consisting of at least one of the cyclohexenylmethyloxabicyclooctanes or intermediates therefor of our invention in the container 212 is accurately controlled so that a temperature in the range of from about 210° F.–275° F. will exist in the conduit 232. The regulation of the temperature through the control 216 and the control 220 is essential in order to ensure temperature balance to provide for the continuous dropping or dripping of molten polymers (e.g., polyolefin) and scenting material containing or consisting of at least one of the cyclohexenylmethyloxabicyclooctanes or intermediates therefor of our invention through the orifices 234 at a rate which will ensure the formation of droplets 236 which fall downwardly onto a moving conveyor belt 238 trained to run between conveyor wheels 240 and 242 beneath the conduit 232.

When the droplets 236 fall onto the conveyor 238, they form pellets 244 which harden almost instanteously and fall off the end of the conveyor 238 into a container 245 which is advantageously filled with water or some other suitable cooling liquid in order to ensure the rapid cooling of each of the pellets. The pellets 244 are then collected from the container 245 and utilized in a process as illustrated infra.

A feature of this aspect of the process of our invention is in the provision for moistening the conveyor belt 238 to ensure rapid formation of the solid polymer (e.g., polyolefin) scented pellets 244 without sticking to the belt. The belt 238 is advantageously of a material which will not normally stick to a melted plastic, but the moistening means 256 ensures a sufficiently cold temperature of the belt surface for the adequate formation of the pellets 244. The moistening means comprises a container 248 which is continuously fed with water 254 to maintain a level for moistening a sponge element 256 which bears against the exterior surface of the belt 238. The container for the moistening means is indicated by reference numeral 250.

THE INVENTION

The instant invention provides cyclohexenylmethyl-oxabicyclooctanes and intermediates therefor defined according to the structures:

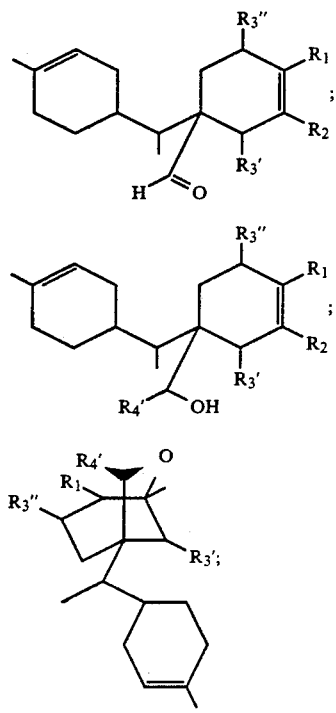

and

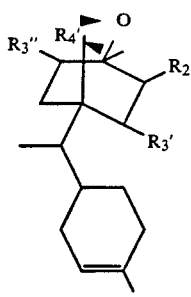

wherein $R_1$, $R_2$, $R_3'$ and $R_3''$ each represents hydrogen or methyl with the provisos:
  (i) one or both of $R_1$ and $R_2$ is methyl;
  (ii) when $R_1$ and $R_2$ are both methyl, then $R_3'$ and $R_3''$ represent hydrogen;
  (iii) one of $R_3'$ and $R_3''$ is methyl and the other of $R_3'$ and $R_3''$ is hydrogen or $R_3'$ and $R_3''$ are both hydrogen; and
  (iv) when $R_3'$ or $R_3''$ is methyl, then $R_1$ is methyl and $R_2$ is hydrogen
and wherein $R_4'$ is hydrogen or $C_1$-$C_5$ alkyl.

The compounds are useful in augmenting or enhancing the aroma of perfume compositions, colognes and perfumed articles (including but not limited to solid or liquid anionic, cationic, nonionic or zwitterionic detergents, fabric softener compositions, perfumed polymers, fabric softener articles, cosmetic powders, hair preparations, and the like). The compounds of our invention are also useful as odor maskants as here and after described in detail.

Thus, the compounds defined according to the genera:

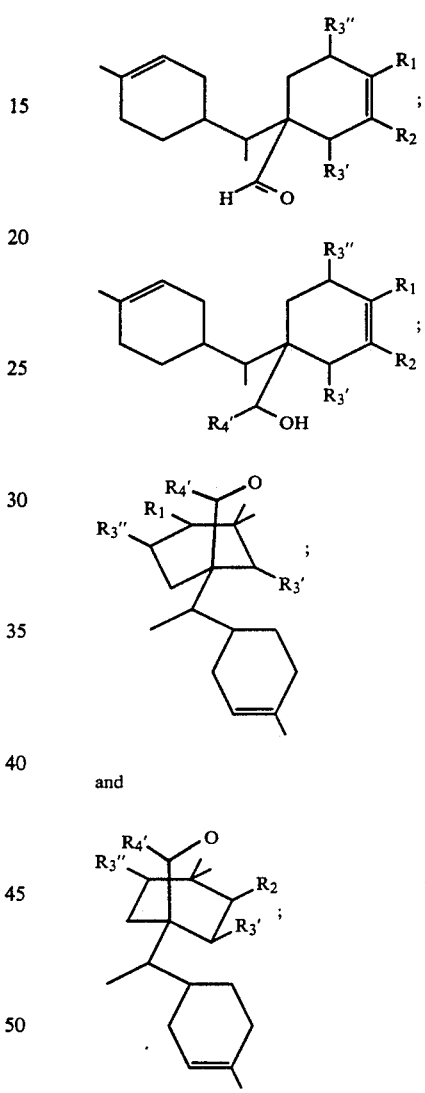

and

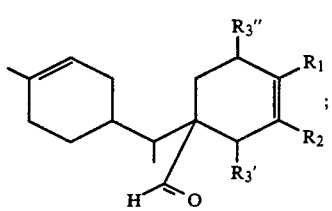

wherein $R_1$, $R_2$, $R_3'$ and $R_3''$ are defined supra augment or enhance earthy, green, animalic and musky aromas with earthy and green topnotes.

The compounds defined according to the genera:

-continued

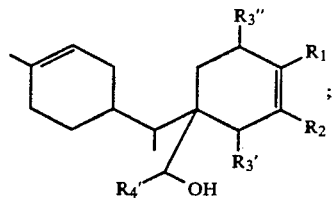

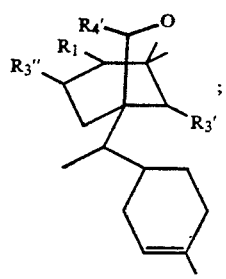

and

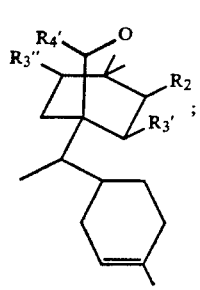

wherein $R_1$, $R_2$, $R_3'$ and $R_3''$ are defined supra may be prepared according to the following reaction sequences:

(A) The compound having the structure:

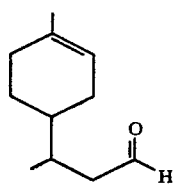

is reacted with formaldehyde according to the reaction:

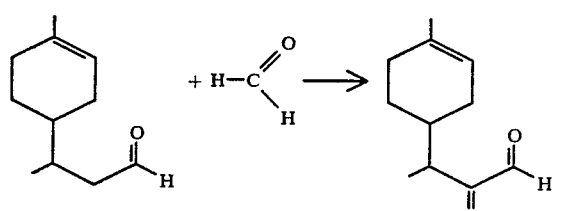

to produce the compound having the structure

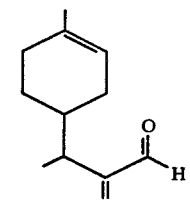

The compound having the structure:

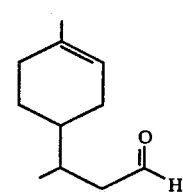

is reacted with a diene defined according to the structure:

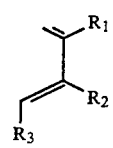

according to the reaction:

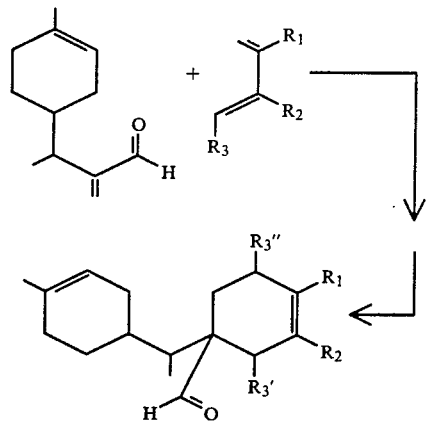

wherein $R_3$ is the same as $R_3'$ or $R_3''$, in order to produce one or more compounds having the structure:

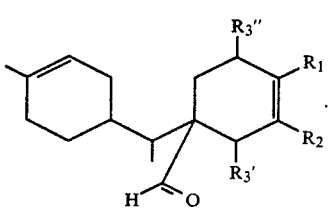

The compound having the structure:

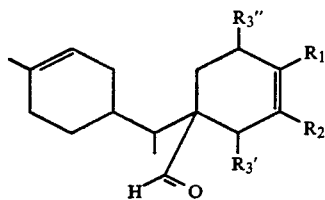

may be used "as is" for its organoleptic properties or it may further be reacted as follows:

(C) One of the compounds defined according to the genus:

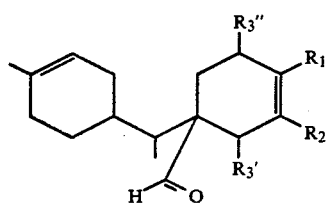

may be then reduced with a reducing agent such as sodium borohydride or VITRIDE ® having the structure:

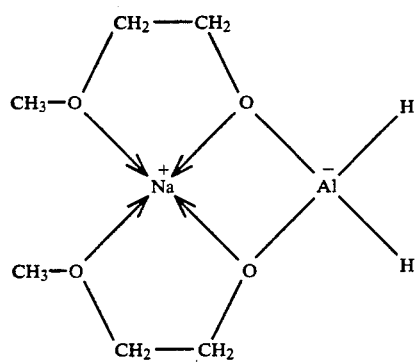

(trademark of the HEXCEL Organization) in order to form one or more members of the genus:

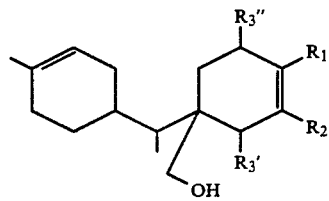

according to the reaction:

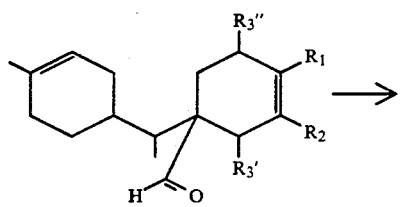 →

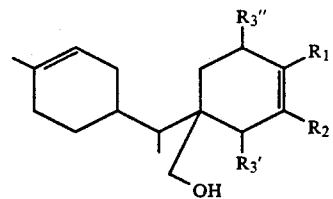

or the compound having the structure:

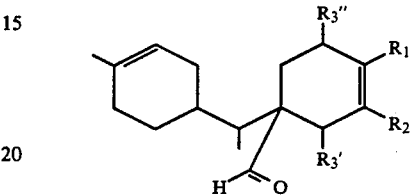

may be reacted with an organometallic compound such as an alkyl lithium or an alkyl Grignard reagent having the structure:

R<sub>4</sub>-M to first yield an organometallic compound having the structure:

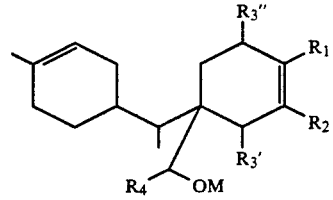

which may be further hydrolyzed to yield the compound having the structure:

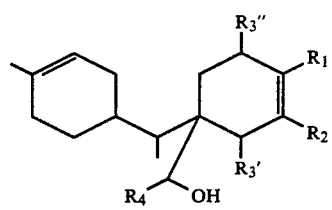

according to the reactions:

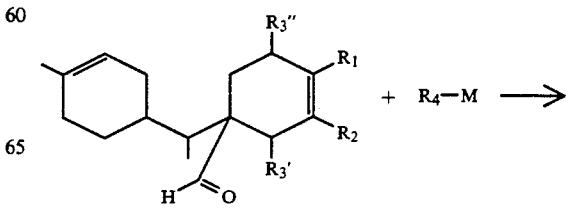

-continued

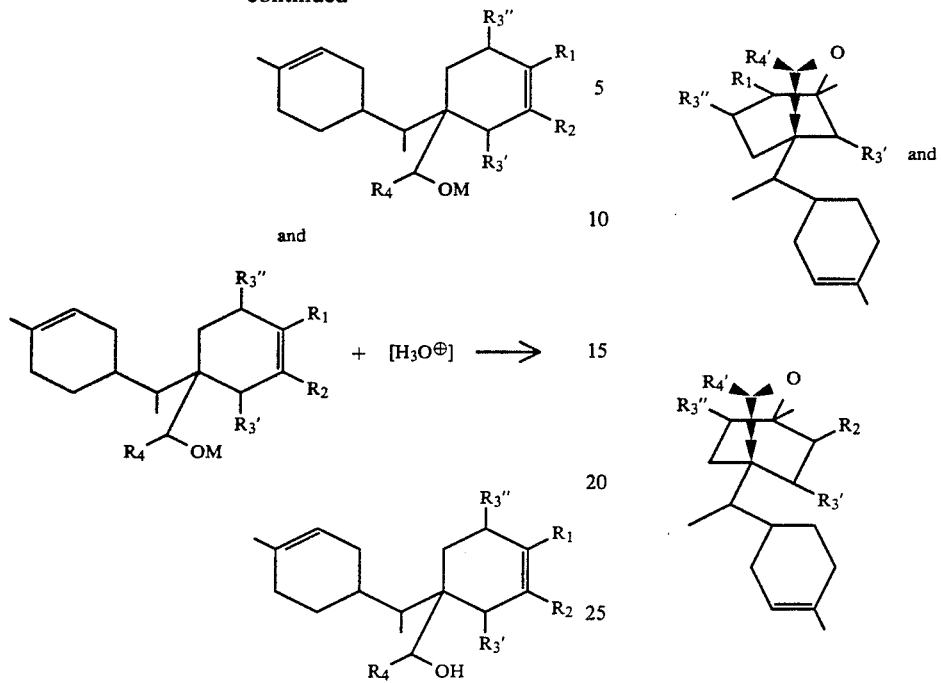

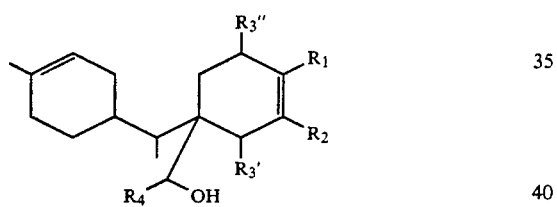

wherein M is Li or MgX wherein X is chloro, bromo or iodo. The compounds defined according to the structure:

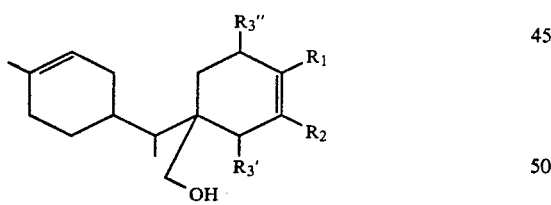

or the compound defined according to the structure:

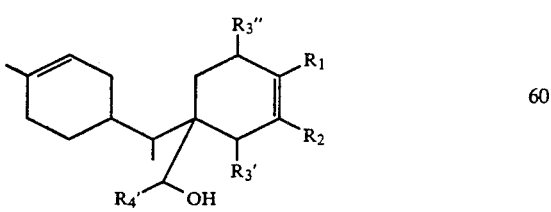

may be used "as is" for their organoleptic properties or they may be further cyclized.

(D) Thus, the compound having the structure:

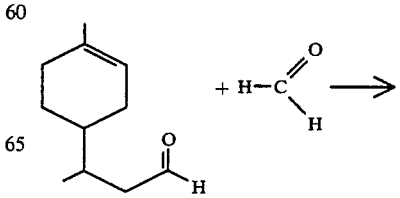

(wherein $R_4'$ is hydrogen or $C_1$-$C_5$ alkyl) may be cyclized to formed the compounds having the structures:

(usually in admixture) according to the reaction:

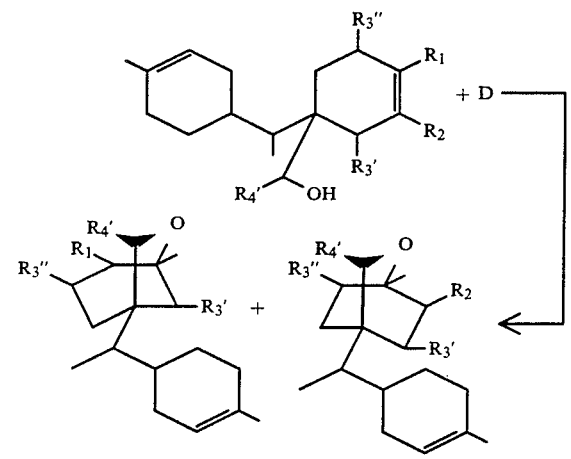

wherein D is a cyclizing agent such as methane sulfonic acid or sulfuric acid.

In the foregoing reaction sequences $R_4$ is $C_1$-$C_5$ alkyl whereas $R_4'$ is hydrogen or $C_1$-$C_4$ alkyl.

With reference to the reaction:

-continued

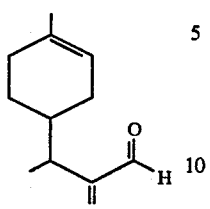

the reaction takes place in the presence of a salt of dibutyl amine and acetic acid, formed from equimolar quantities of dibutyl amine and acetic acid. The mole ratio of formaldehyde: compound having the structure:

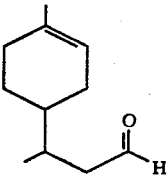

may vary from about 0.5:1 up to about 1:0.5 with a preferred excess of compound having the structure:

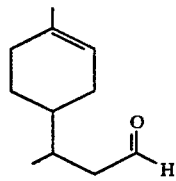

in the reaction. The reaction temperature may vary from about 60° C. up to about 80° C. At the end of the reaction, the reaction product having the structure:

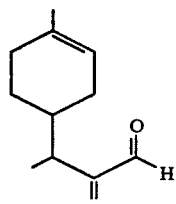

is recovered by fractional vacuum distillation.

With respect to generic reaction:

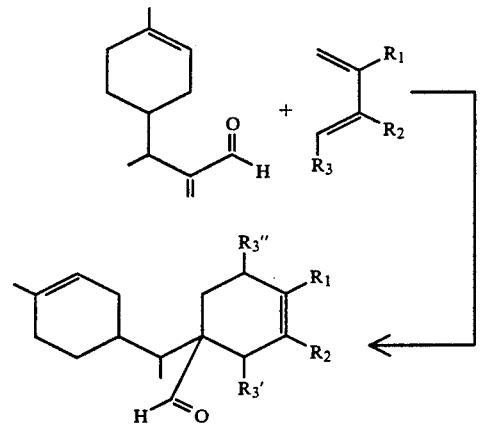

the reagent having the structure:

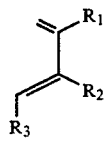

may be one of the compounds:

or

or a mixture of two or more of said dienes.

The Diels-Alder reaction of the unsaturated aldehyde having the structure:

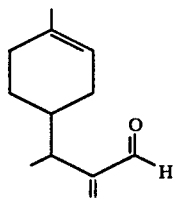

with the diene having the structure:

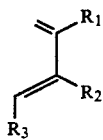

is a procedure well known in the prior art as is set forth at lines 25-34, column 11 of U.S. Letters Pat. No. 4,301,018 the specification for which is incorporated by reference herein. The reaction may be carried out in the presence of a Lewis acid catalyst such as zinc chloride, aluminum chloride or aluminum bromide or it may be carried out in the absence of catalysts at higher temperatures, e.g., 50° C. up to 150° C. When carrying out the Diels-Alder reaction in the presence of catalysts, lower temperatures, e.g., 10° C. up to +30° C. may be utilized.

In carrying out the Diels-Alder reaction, that is preferable to carry out same using a high pressure apparatus such as a Parr Bomb using a reaction pressure of between 100 and 800 psig.

An example of the foregoing Diels-Alder reaction is one taking place between isoprene and the compound having the structure:

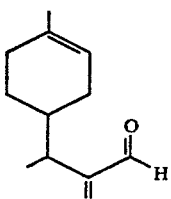

wherein the by-product having the structure:

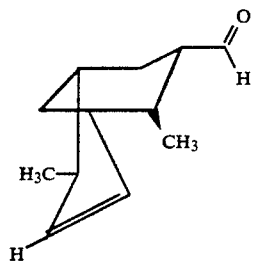

is formed according to the reaction:

At the end of the reaction, the reaction product defined according to the structure:

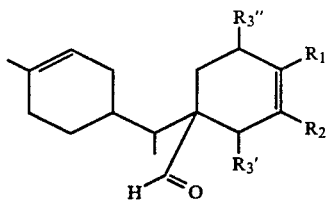

may be used "as is" for its organoleptic properties or it may be further reacted. In any event the resulting product is preferably fractionally distilled to yield a more refined version of the product.

When the resulting product is "reduced" according to the reaction:

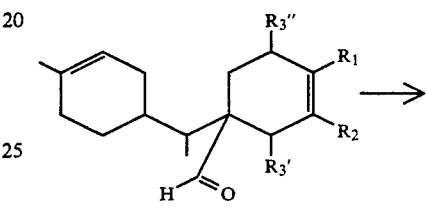

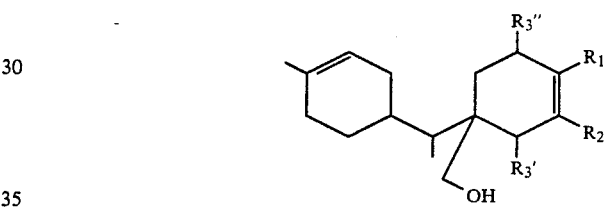

the reducing agent is a selective reducing agent to wit:
lithium aluminumhydride;
sodium borohydride;

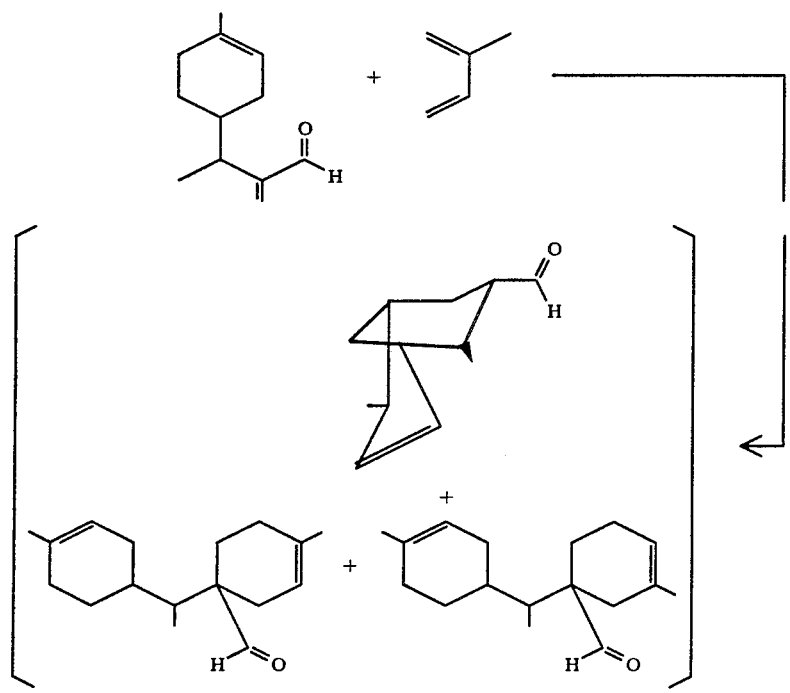

potassium borohydride;
lithium aluminumhydride or
VITRIDE°
having the structure:

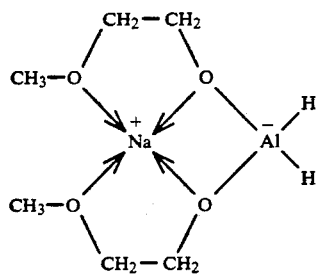

(VITRIDE° is a registered trademark of HEXCEL Organization defining the compound having the aforementioned structure).

The reduction reaction will be carried out in the presence of an inert solvent such as anhydrous ethanol or isopropyl alcohol or anhydrous methanol. The reaction is carried out at temperatures of between 20° C. up to about 50° C. for a period of time of from about two hours up to about ten hours. The weight ratio of reducing agent, such as alkali metal borohydride:aldehyde is from about 1:20 up to about 1:5 with a ratio of reducing agent:aldehyde of 1:12 being preferred and a reaction temperature of from about 25° C. up to about 45° C. being preferred. The concentration of aldehyde and solvent may vary from about 1 part aldehyde:0.5 parts solvent up to about 1 part aldehyde:4 parts solvent with a preferred ratio of 180 grams of aldehyde:100ml solvent.

On the other hand when the aldehyde having the structure:

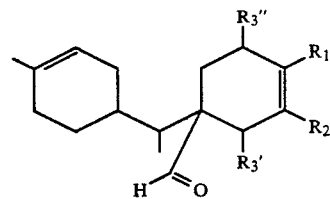

is subjected to electrophilic addition according to the reaction sequence:

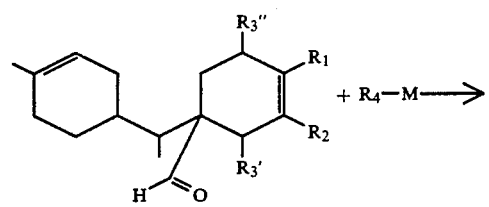

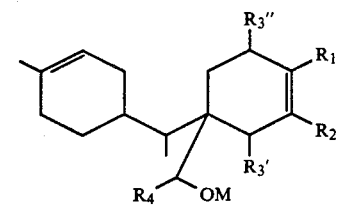

and

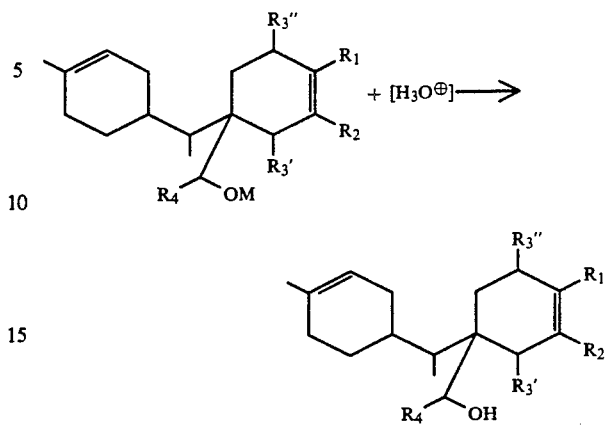

The reagent having the structure:

$R_4$-M may be a $C_1$-$C_5$ alkyl lithium or a $C_1$-$C_5$ Grignard reagent for example methyl magnesium chloride, methyl magnesium bromide, methyl magnesium iodide, methyl lithium, ethyl magnesium chloride, n-propyl magnesium bromide, n-butyl lithium, n-butyl magnesium chloride or n-pentyl lithium. Thus, in forming a Grignard reagent, a $C_1$-$C_5$ alkyl halide is reacted with magnesium where the mole ratio of alkyl halide:magnesium in order to form the Grignard reagent is from about 0.9:1 up to about 1.5:1. The mole ratio of alkyl halide to aldehyde in the subsequent reaction varies from 0.8:1 up to about 1.5:1. This reaction of the Grignard reagent with the aldehyde takes place in an ether solvent such as diethyl ether, tetrahydrofuran or di-n-butyl ether or another inert solvent such as toluene, chloroform or benzene to which two equivalents of ether has been added. The temperature of reaction preferably is between 0 and 100° C. with the most preferred temperature range for this reaction being from 35° C. up to 45° C.

The resulting organometallic compound defined according to the structure:

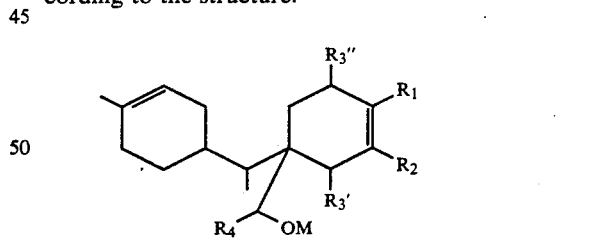

wherein $R_1$, $R_2$, $R_3'$, $R_3''$, $R_4$ and M have been defined as supra, is then hydrolyzed in the presence of acid such as aqueous hydrochloric acid or aqueous ammonium chloride. The hydrolysis reaction to wit:

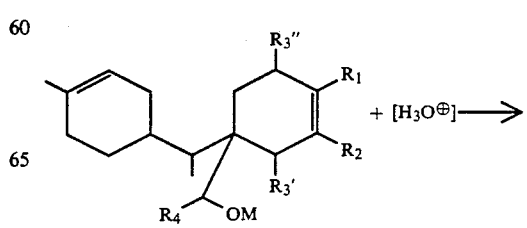

-continued

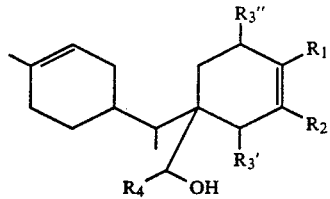

yields the compound having the structure:

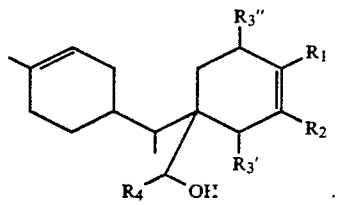

The compound having the structure:

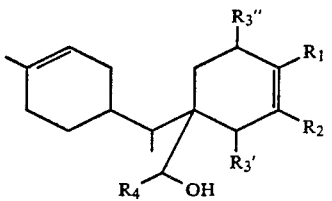

where the compound having the structure:

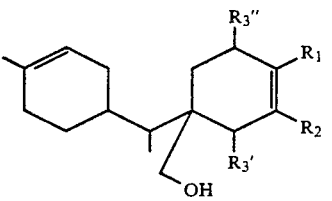

may be used "as is" for their organoleptic properties or such compounds may be cyclized subsequent to fractional distillation. The cyclization reaction to wit:

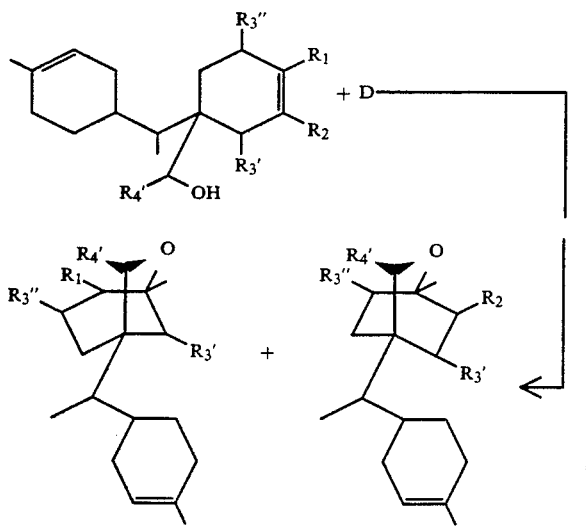

wherein D is a cyclizing agent takes place at a temperature in the range of from about 25° C. up to 150° C. in the presence of an acid such as aqueous hydrochloric acid, sulfuric acid, phosphoric acid or methane sulfonic acid. This acid may be used in combination with an alcohol such as isopropyl alcohol or with some other solvents such as tetrahydrofuran, acrylonitrile, nitrile methane or 2-nitropropane; or the acid may be used by itself to effect the cyclization. The cyclization may also be carried out using a Lewis acid catalyst such as borontrifluoride etherate, aluminum trichloride, zinc chloride, stannic chloride or zinc bromide in the presence of a solvent such as toluene, chloroform or xylene.

The formation of the alcohols having the structure:

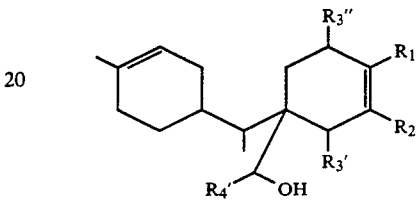

and the oxybicyclooctane derivatives having the structures:

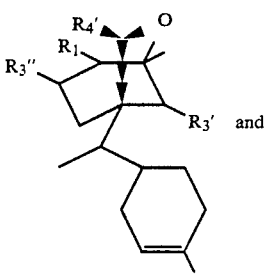

and

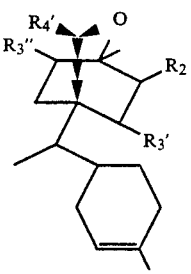

may be carried out as a "one step" reaction of a "two step" reaction. In carrying out the "two step" reaction whereby the cyclohexene carbinol is first isolated and then cyclized, the reaction to form the cyclohexene carbinol from the cyclohexene carboxaldehyde and the cyclization reaction are all carried out by separate vessels. However, in the "one step" reaction the reaction of the cyclohexene carboxaldehyde to form the cyclohexene carbinol followed by cyclization may take place in a single reactor without separation of the cyclohexene carbinol. The conditions for the "one step" and "two step" processes are substantially the same.

The following Table I sets forth examples of the cyclohexenylmethyloxabicyclooctanes of our invention and their organoleptic characteristics:

TABLE I

| Structure of Compounds | Fragrance Characteristics |
|---|---|
| Mixture of compounds having the structures: 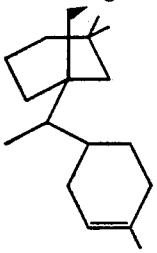 <br>and<br> 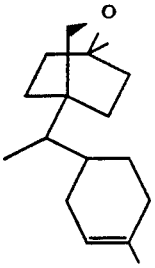 <br>produce according to Example IV, bulked distillation fractions 8 and 9. | An earthy and green aroma with earthy and green topnotes. |
| Mixture of compounds having the structures: 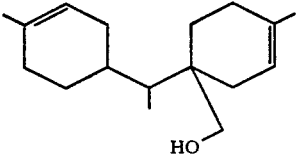 <br>and<br> 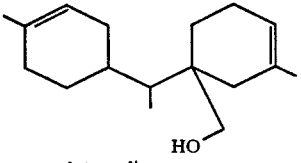 <br>prepared according to Example III, fraction 12. | An animalic and musky aroma. |

At least one of the cyclohexenylmethyloxabicyclooctanes or intermediates therefor and one or more auxiliary perfume ingredients including, for example, alcohols (other than the alcohol intermediate of our invention), aldehydes (other than the aldehyde intermediate of our invention), ketones, terpinic hydrocarbons, nitriles, esters, ethers (other than the cyclohexenylmethyloxabicyclooctanes of our invention), lactones, natural essential oils and synthetic essential oils, may be admixed so that the combined odors of the individual components produce a pleasant and desired fragrance, particularly in the pine fragrance area. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however, the over-all sensory effect of the perfume composition will be at least the sum total of the effects of each of the ingredients. Thus, at least one of the cyclohexenylmethyloxabicyclooctanes or intermediates therefor of our invention can be used to alter, modify or enhance the aroma characteristics of a perfume composition, for example, by utilizing or moderating the olfactory reaction contributed by another ingredient in the composition.

The amount of one or more of the cyclohexenylmethyloxabicyclooctanes or intermediates therefor of our invention which will be effective in perfume compositions as well as in perfumed articles and colognes depends on many factors, including the other ingredients, their amounts and the effects which are desired. It has been found that perfume compositions containing as little as 0.01% of at least one of the cyclohexenylmethyloxabicyclooctanes or intermediate therefor of our invention or even less (e.g., 0.005%) can be used to impart, augment or enhance earthy, green, animalic and musky aromas with earthy and green topnotes to soaps, cosmetics, solid or liquid, anionic, cationic, nonionic or zwitterionic detergents, fabric softener compositions, fabric softener articles, hair preparations and perfumed polymers. The amount employed can range up to 70% of the fragrance components and will depend on considerations of cost, nature of the end product, the effect desired on the finished product and the particular fragrance sought.

One or more of the cyclohexenylmethyloxabicyclooctanes or intermediates therefor of our invention are useful [taken alone or together with other ingredients in perfumed compositions] as (an) olfactory component(s) in detergents and soaps, space odorants and deodorants, perfumes, colognes, toilet water, bath preparations such as creams, deodorants, hand lotions and sunscreens, powders such as talcs, dusting powders, face powders and the like. When used as (an) olfactory component(s) as little as 1% of at least one of the cyclohexenylmethyloxabicyclooctanes or intermediates therefor of our invention or even less will suffice to impart intense long-lasting earthy, green, animalic and musky aromas with earthy and green topnotes to pine formulations. Generally, no more than 20% of at least one of the cyclohexenylmethyloxabicyclooctanes or intermediates therefor of our invention based on the ultimate end product is required in the perfume composition.

Accordingly, in perfume compositions and colognes from about 0.01% up to about 70% of the perfume composition may be at least one of the cyclohexenylmethyloxabicyclooctanes or intermediates therefor of our invention. In perfumed articles, the quantity of at least one of the cyclohexenylmethyl oxabicyclooctanes or intermediates therefor of our invention in the perfumed article may vary from about 0.005% up to about 25% of the perfumed article in the case of perfumed polymers, for example, and up to about 8% in the case of solid or liquid anionic, cationic, nonionic or zwitterionic detergents, for example.

In addition, the perfume composition or fragrance composition of our invention can contain a vehicle, or carrier for at least one of the cyclohexenylmethyloxabicyclooctanes or intermediates therefor of our invention. The vehicle can be a liquid such as a non-toxic alcohol, such as ethyl alcohol or a non-toxic glycol, such as propylene glycol or the like. The carrier can also be an absorbent solid, such as a gum (e.g., gum arabic xanthan gum, or guar gum or mixtures of same) or components for encapsulating the composition (such as gelatin as by means of coacervation or such as an ureaformaldeyde prepolymer when such a polymeric wall is formed around a liquid perfume composition center).

The following Examples I-IV serve to illustrate the processes for preparing the compounds of our invention and compounds useful for their organoleptic properties. Examples following Examples IV (Examples V, et seq.) illustrate organoleptic utilities of the cyclohexenylmethyloxabicyclooctanes or intermediates therefor of our invention.

All parts and percentages given herein are by weight unless otherwise specified.

EXAMPLE I

PREPARATION OF ALPHA METHYLENE LIMONENE

Reaction:

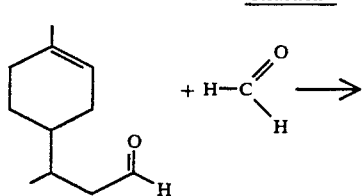

Into a twelve liter flask equipped with stirrer, thermometer, reflux condenser, heating mantle and addition funnel is placed 81 grams (0.625 moles) of dibutyl amine and 81 grams (0.625 moles) of acetic acid. The reaction mass temperature rises to 50° C. While maintaining the reaction mass at 28-42° C., rapidly, 1,457 grams (17.97 moles) 37% formaldehyde is added to the reaction mass.

Over a five hour period while maintaining the reaction mass at 70° C., 1,989 grams (11.98 moles) of the compound having the structure:

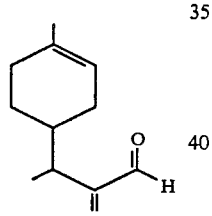

is added to the reaction mass. The reaction mass is then aged for 5.5 hours with stirring at 70° C. and is then permitted to cool for a period of 12 hours. At the end of the reaction the reaction mass now exists in two phases. The organic phase is separated from the aqueous phase and the organic phase is washed with the following:

(a) 1 liter of water (b) two 500 ml portions of saturated sodium bicarbonate; and (c) two 1000 ml portions of saturated sodium chloride.

The organic phase is then dried over an anhydrous magnesium sulfate, filtered and distilled to yield 1,339 grams of product (63% yield). The distillation fractions are as follows:

| Fraction No. | Vapor Temp. (°C.) | Liquid Temp. (°C.) | Vacuum mm/Hg. Pressure |
|---|---|---|---|
| 1 | 48/98 | 110/110 | 3.52/3.46 |
| 2 | 95 | 115 | 2.25 |
| 3 | 115 | 200 | 2.7 |

Figure 1:
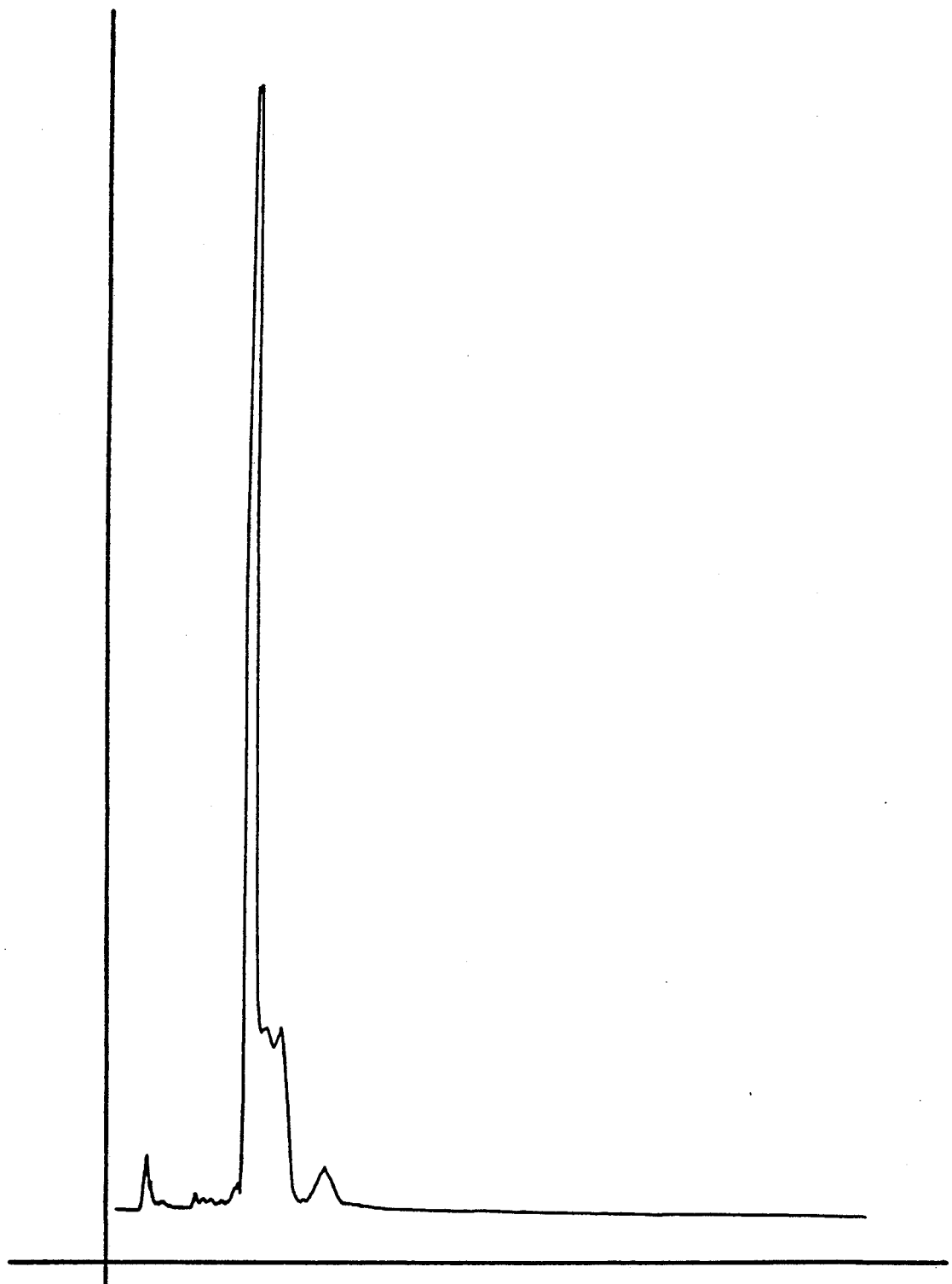
FIG. 1 is the GLC profile for the reaction product of Example I containing the compound having the structure.

FIG. 1 is the GLC profile for the crude reaction product (Conditions:Carbowax column programmed at 220° C. isothermal).

FIG. 2 is the NMR spectrum for the compound having the structure:

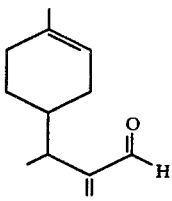

EXAMPLE II

PREPARATION OF SUBSTITUTED CYCLOHEXENYLMETHYLFORMYLCYCLOHEXENE

Reaction:

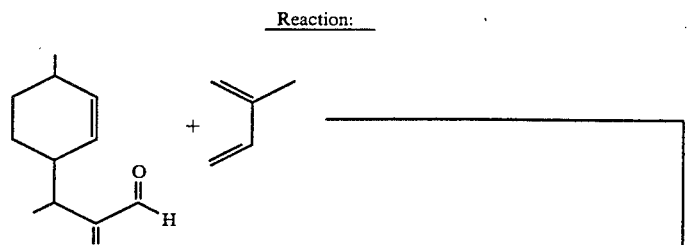

-continued

Reaction:

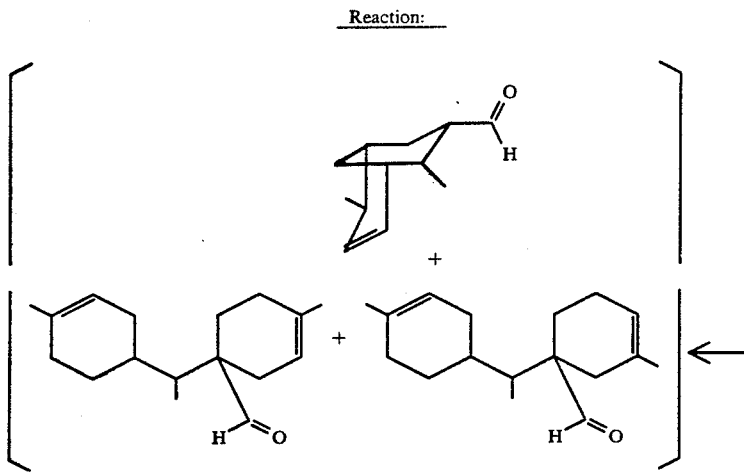

Into a 2 liter Parr Bomb are placed 367 grams (5.39 moles) of isoprene having a structure:

and 800 grams (4.50 moles) of the compound having the structure:

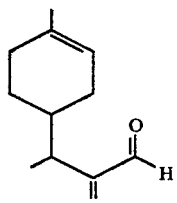

prepared according to Example I. The Parr Bomb is closed and sealed and the reaction mass is heated 150° C. and maintained at 150° C. for a period of 3 hours. The reaction mass is then heated to 170° C. and aged for a period of 8 hours. The reaction mass is cooled and the Parr Bomb is then opened. The reaction mass is then filtered and distilled on a fractional distillation column yielding the following fractions:

| Fraction No. | Vapor Temp. (°C.) | Liquid Temp. (°C.) | Vacuum mm/Hg. Pressure |
|---|---|---|---|
| 1 | 28/65 | 67/90 | 7.25/2.63 |
| 2 | 67 | 92 | 2.21 |
| 3 | 72 | 95 | 2.14 |
| 4 | 96 | 119 | 1.94 |
| 5 | 104 | 121 | 1.85 |
| 6 | 107 | 125 | 1.75 |
| 7 | 110 | 125 | 1.69 |
| 8 | 115 | 136 | 1.63 |
| 9 | 130 | 147 | 1.60 |
| 10 | 138 | 153 | 1.63 |
| 11 | 145 | 158 | 1.85 |
| 12 | 162 | 210 | 2.71 |

The resulting product weighs 961 grams. Of this 961 grams, 490 grams are the mixture of compounds having the structures:

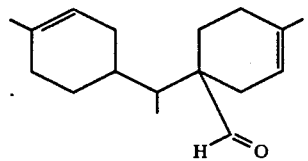

and

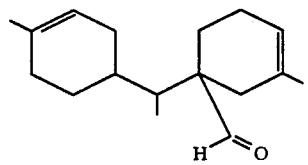

The remainder is the product having the structure:

FIG. 3 is the GLC profile of the reaction mass prior to distillation (Conditions:Carbowax column programmed at 220° C. isothermal).

FIG. 4 is the NMR spectrum for the mixture of compounds having the structures:

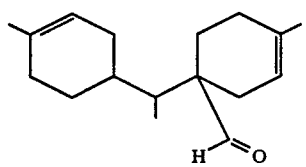

and

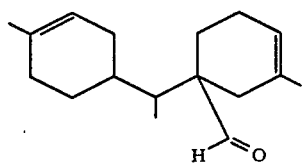

EXAMPLE III

PREPARATION OF SUBSTITUTED CYCLOHEXENYLMETHYLHYDROXYMETHYL CYCLOHEXENE

Reaction:

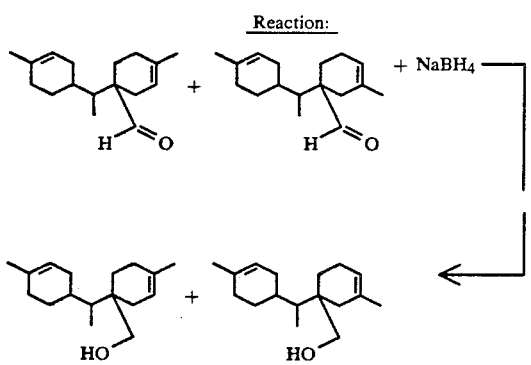

Into a 5 liter reaction flask equipped with stirrer, thermometer, a reflux condenser and heating mantle and addition funnel are placed 115 grams (1.70 moles) of sodium borohydride and 1,600 mls of a 50:50 mixture of isopropyl alcohol and water. The reaction mass is stirred and maintained at 26° C. Over a period of 4 hours, 837 grams of the mixture of compounds having the structures:

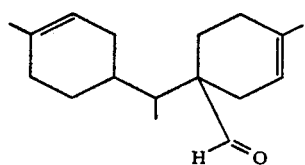

and

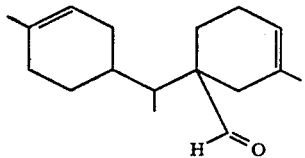

prepared according to Example II is added to the reaction mass. The reaction mass temperature is raised to 40° C. and maintained at 40° C. with stirring for a period of 1.5 hours. At the end of the 1.5 hour period, the organic phase is separated from the aqueous phase and the organic phase is washed with 400 ml saturated sodium chloride.

The organic phase is then dried over anhydrous magnesium sulfate and distilled to yield 680 grams of product.

The following are the distillation fractions:

| Fraction No. | Vapor Temp. (°C.) | Liquid Temp. (°C.) | Vacuum mm/Hg. Pressure |
|---|---|---|---|
| 1 | 65/126 | 78/170 | ATM/1.47 |
| 2 | 140 | 170 | 1.46 |
| 3 | 145 | 173 | 1.36 |
| 4 | 148 | 173 | 1.36 |
| 5 | 152 | 175 | 1.33 |
| 6 | 154 | 175 | 1.32 |
| 7 | 154 | 175 | 1.32 |
| 8 | 154 | 177 | 1.32 |
| 9 | 155 | 178 | 1.30 |
| 10 | 158 | 178 | 1.30 |
| 11 | 155 | 180 | 1.32 |
| 12 | 155 | 190 | 1.31 |
| 13 | 159 | 211 | 1.34 |
| 14 | 150 | 230 | 1.34 |

Fraction 12 has an animalic and musky aroma. Fraction 12 consists of the compounds having the structure:

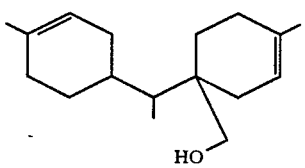

and

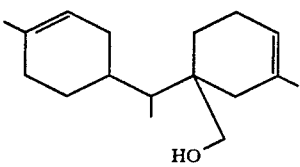

FIG. 5 is the GLC profile for the reaction product prior to distillation (Conditions:SE-30 column programmed at 220° C. isothermal).

FIG. 6 is the NMR spectrum for the mixture of compounds having the structures:

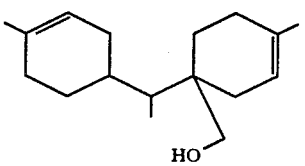

and

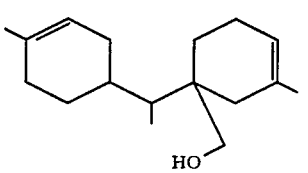

EXAMPLE IV

PREPARATION OF SUBSTITUTED CYCLOHEXENYLMETHYLOXABICYCLOOCTANE

Reaction:

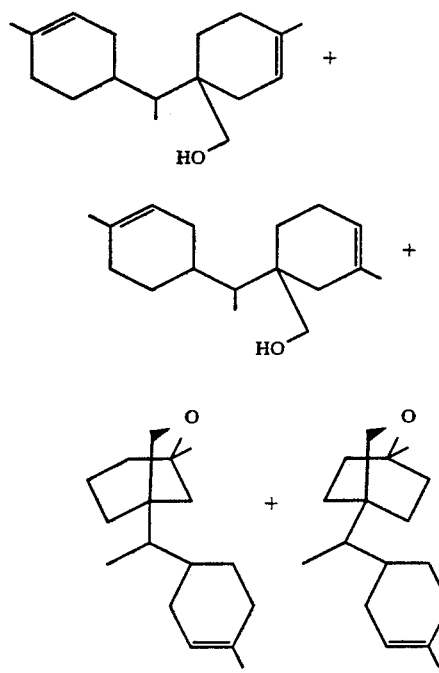

Into a 2 liter reaction flask equipped with stirrer, thermometer, reflux condenser, heating mantle and addition funnel are placed 405 grams (1.63 moles) of the mixture of compounds having the structures:

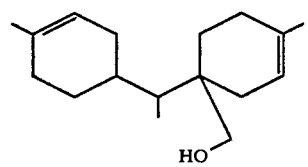

and

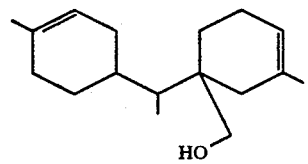

(bulked distillation fractions 10–13) produced according to Example III and 400 ml nitromethane. With stirring the reaction mass is maintained at 26° C. while adding 7.84 grams (0.082 moles) of methane sulfonic acid.

The reaction mass is then heated to 80° C. and maintained at 80° C. with stirring for a period of 2 hours. At the end of the 2 hour period the reaction mass is cooled to room temperature.

One liter of toluene is added to the reaction mass and the reaction mass now exists in two phases; an organic phase and a aqueous phase. The layers are separated and the organic phase is washed with 350 ml of 10% sodium bicarbonate followed by two 300 ml portions of saturated sodium chloride.

The organic phase is then dried over anhydrous magnesium sulfate and filtered.

The resulting product is then fractionally distilled yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 42/43 | 46/83 | 90/0.850 | A |
| 2 | 136 | 157 | 1.15 | 3 |
| 3 | 139 | 157 | 1.12 | 7 |
| 4 | 139 | 155 | 1.11 | 9.5 |
| 5 | 138 | 155 | 1.11 | 11 |
| 6 | 140 | 155 | 1.13 | 10.4 |
| 7 | 140 | 155 | 1.11 | 9.5 |
| 8 | 140 | 156 | 1.11 | 11 |
| 9 | 140 | 160 | 1.13 | 24 |
| 10 | 140 | 170 | 1.12 | 8.0 |
| 11 | 135 | 205 | 1.07 | 5 |

Bulked distillation fractions 8 and 9 have an earthy and green aroma with earthy and green topnotes.

The resulting product contains two compounds having the structures:

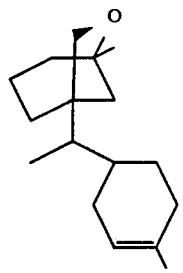

and

with the ratio of the compound having the structure:

to the compound having the structure:

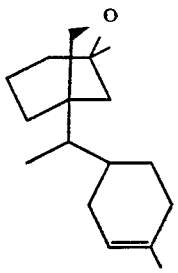

being 2:1.

FIG. 7 is the GLC profile for the reaction product containing the compounds having the structures:

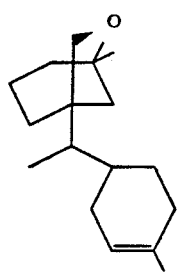

and

prior to distillation (Condition:SE-30 column programmed at 220° C. isothermal).

FIG. 8 is the NMR spectrum for the mixture of compounds having the structures:

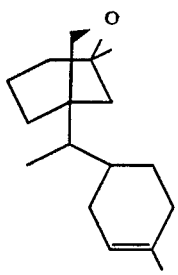

and

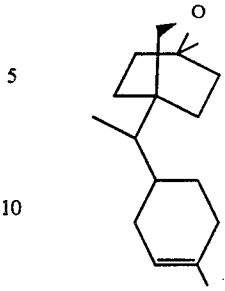

-continued

EXAMPLE V

The following pine fragrance formulations are prepared:

| INGREDIENTS | PARTS BY WEIGHT | |
|---|---|---|
|  | VA | VB |
| Isobornyl acetate | 100 | 100 |
| Camphor | 10 | 10 |
| Terpineol | 25 | 25 |
| Fir Balsam Absolute (50% in Diethyl Phthalate) | 20 | 20 |
| Courmarin | 4 | 4 |
| Linalool | 30 | 30 |
| Anethol | 2 | 2 |
| Fenchyl Alcohol | 10 | 10 |
| Lemon Terpenes Washed | 50 | 50 |
| Borneol | 5 | 5 |
| Galbanum Oil | 5 | 5 |
| Turpentine Russian | 150 | 150 |
| Pinus Pumilionus | 50 | 50 |
| Eucalyptol | 50 | 50 |
| 2,2,6-trimethyl-1-cyclo hexene-1-carboxaldehyde | 5 | 5 |
| Maltol 1% in Diethyl Phthalate | 5 | 5 |
| Mixture of compounds having the structures: | 12 | 0 |

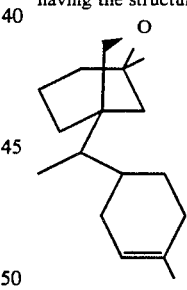

and

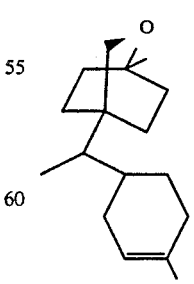

prepared according Example IV (bulked distillation fractions 8 and 9.

| Mixture of compounds having the structures: | 0 | 12 |

-continued

| INGREDIENTS | PARTS BY WEIGHT | |
|---|---|---|
| | VA | VB |
| 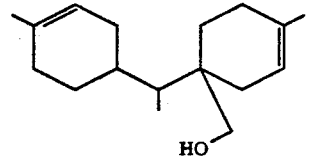 and 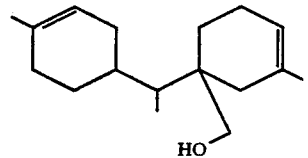 prepared according to Example III (distillation fraction 12) | | |

The pine fragrance has imparted thereto an earthy and green undertone and earthy and green topnotes as a result of adding thereto the mixture of compounds having the structures:

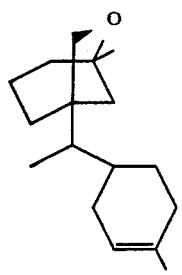

and

prepared according to Example IV. Accordingly, the fragrance of Example VA can be described as "piney with earthy and green undertones and earthy and green topnotes".

The mixture of compounds having the structures:

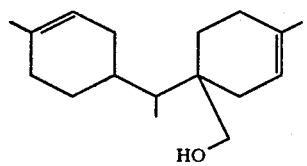

and

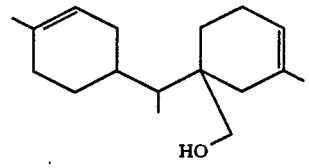

imparts to the pine fragrance animalic and musky undertones. Accordingly, the pine fragrance of Examples VB can be described as "piney with musky and animalic undertones".

EXAMPLE VI

A COSMETIC POWDER PREPARATION

A cosmetic powder is prepared by mixing in a ball mill 100 grams of talcum powder with 0.25 grams of one of the substances set forth in Table II below containing at least one of the cyclohexenylmethyloxabicyclooctanes or intermediates therefor for our invention. Each of the cosmetic powders has an excellent aroma as described in Table II below:

TABLE II

| PERFUMERY SUBSTANCE | AROMA NUANCE |
|---|---|
| Mixture of compounds having the structures: 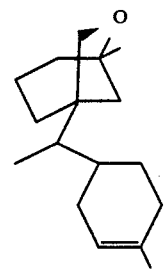 and 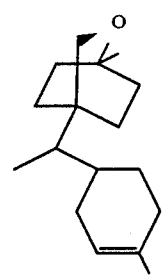 prepared according to Example IV, bulked distillation fractions 8 and 9. | An earthy and green aroma with earthy and green topnotes. |
| Mixture of compounds the structures: 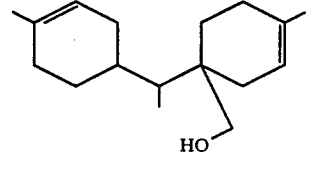 and | An animalic and musky aroma. |

TABLE II-continued

| PERFUMERY SUBSTANCE | AROMA NUANCE |
|---|---|
| [structure with HO group] prepared according to Example III, distillation fraction 12. | |
| Perfume compositions of Example VA | Piney with earthy and green undertones and earthy and green topnotes. |
| Perfume compositions of Example VB | Piney with musky and animalic undertones |

EXAMPLE VII

PERFUMED LIQUID DETERGENT

Concentrated liquid detergent (Lysine salt of n-dodecylbenzene sulfonic acid as more specifically described in U.S. Pat. No. 3,948,818 issued on Apr. 6, 1976, the specification for which is incorporated herein) with aromas as set forth in Table II of Example VI, supra are prepared containing 0.10%, 0.15%, 0.20%, 0.25%, 0.30% and 0.35% of each of the substances of Table II of Example VI. They are prepared by adding and homogeneously admixing the appropriate quantity of one of the substances of Table II of Example VI in the liquid detergent. The detergents all possess excellent aromas as set forth in Table II of Example VI.

EXAMPLE VIII

PREPARATION OF A COLOGNE AND HANDKERCHIEF PERFUME

The substances set forth in Table II of Example VI are incorporated separately into colognes at concentrations of 2.0%, 2.5%, 3.0%, 3.5%, 4.0%, 4.5% and 5.0% in 75%, 80%, 85%, and 90% aqueous food grade ethanol solutions of 15%, 20%, 25% and 30%, in 80%, 85%, 90% and 95% aqueous food grade ethanol solutions. Distinctive aromas as set forth in Table II of Example VI, supra are imparted to the colognes and to the handkerchief perfume compositions at all levels indicated.

EXAMPLE IX

PREPARATION OF SOAP COMPOSITION

One hundred grams of soap chips (IVORY ®, produced by the Procter & Gamble Company, of Cincinnati, Ohio) are admixed with 1 gram of each of the substances of Table II of Example VI, supra until homogeneous compositions are obtained. The homogeneous compositions are each separated then heated under 3 atmospheres pressure at 180° C. for a period of 3 hours and the resulting liquid samples are placed in soap molds. The resulting soap cake, on cooling, manifests excellent long-lasting aromas as set forth in Table II of Example VI, supra.

EXAMPLE X

PREPARATION OF SOLID DETERGENT COMPOSITIONS

Detergents are prepared from the following ingredients according to Example II of Canadian Letters Patent No. 1,007,948 the specification for which is incorporated by reference herein:

| INGREDIENTS | PARTS BY WEIGHT |
|---|---|
| Neodol ® 45-11 (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. A total of 100 grams of said detergent is admixed separately with 0.10, 0.15, 0.20 and 0.25 grams of each of substances of Table II of Example VI. Each of the detergent samples has an excellent aroma as set forth in Table II of Example VI.

EXAMPLE XI

DRYER-ADDED FABRIC. SOFTENER ARTICLE

Utilizing the procedure of Example II at column 15 of U.S. Letters Pat. No. 3,623,396, the specification for which is incorporated by reference herein, a non-woven cloth substrate useful as a dryer-added fabric softening article of manufacture is prepared wherein the substrate, the substrate coating and the outer and the perfuming material are as follows:

1. A water "dissolvable" paper ("Dissolvo Paper")
2. Adogen 448 (m.p. about 140° F) as the substrate coating; and
3. An outer coating having the following formulation (m.p. about 150° F.):
   57% $C_{20-22}$ HAPS
   22% isopropyl alcohol
   20% antistatic agent
   1% of one of the substances of Table II of Example VI, supra Fabric softening compositions containing one of the substances of Table II of Examples VI consist essentially of a substrate having a weight of about 3 grams per 100 square inches of substrate coating having a weight of about 1.85 grams per 100 square inches; and an outer coating having a weight of about 1.4 grams per 100 square inches thereby providing a total aromatized substrate and outer coating weight ratio of about 1 by weight of the substrate.

Pleasant aromas as set forth in Table II of Example VI are imparted to the head space in the dryer on operation thereof using the said drier-added fabric softening non-woven fabric.

What is claimed is:

1. A cyclohexenylmethyloxabicyclooctane or intermediate therefor defined according to the structures selected from the group consisting of:

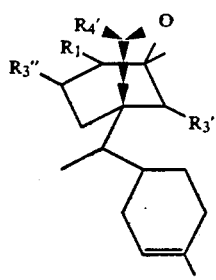

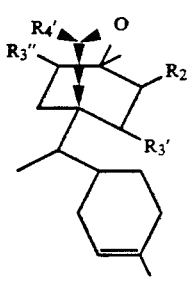

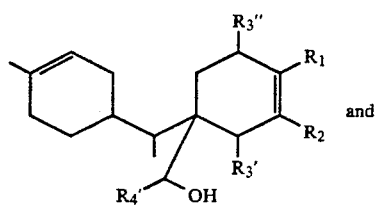

and

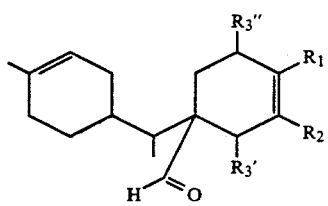

wherein $R_1$, $R_2$, $R_3'$ and $R_3''$ each represents hydrogen or methyl with the provisos:

(i) one or both of $R_1$ and $R_2$ is methyl;

(ii) when $R_1$ and $R_2$ are both methyl, then $R_3'$ and $R_3''$ are each hydrogen;

(iii) one of $R_3'$ and $R_3''$ is methyl and the other is hydrogen or $R_3'$ and $R_3''$ are both hydrogen; and (iv) when $R_3'$ or $R_3''$ is methyl then $R_1$ is methyl and $R_2$ is hydrogen;

2. The composition of claim 1 compromising the mixture of compounds having the structures:

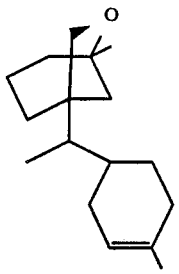

and

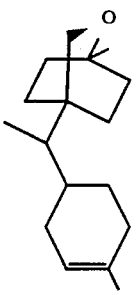

3. The composition of claim 1 comprising the mixture of compounds having the structures:

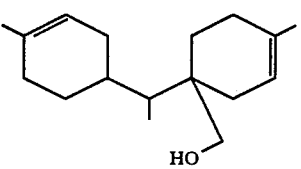

and

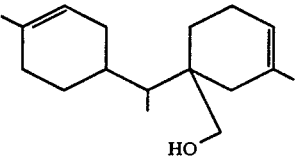

4. The composition of claim 1 comprising the mixture of compounds having the structures:

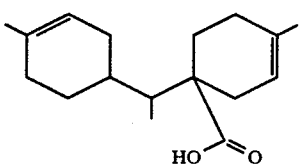

and

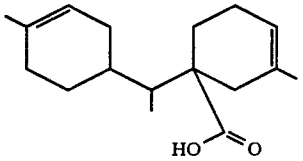

* * * * *